US012702213B2

(12) United States Patent
Levy

(10) Patent No.: US 12,702,213 B2
(45) Date of Patent: *Aug. 11, 2026

(54) HAND HELD DERMAPLANING DEVICE AND DERMAPLANING PROCESS

(71) Applicant: DD Karma LLC, Chicago, IL (US)

(72) Inventor: Dara Levy, Highland Park, IL (US)

(73) Assignee: DD Karma LLC, Chicago, IL (US)

( * ) Notice: Subject to any disclaimer, the term of this patent is extended or adjusted under 35 U.S.C. 154(b) by 70 days.

This patent is subject to a terminal disclaimer.

(21) Appl. No.: 18/774,232

(22) Filed: Jul. 16, 2024

(65) Prior Publication Data

US 2024/0365950 A1 Nov. 7, 2024

Related U.S. Application Data

(60) Division of application No. 17/198,446, filed on Mar. 11, 2021, now Pat. No. 12,507,783, which is a (Continued)

(51) Int. Cl.
*A45D 44/22* (2006.01)
*A45D 26/00* (2006.01)
(Continued)

(52) U.S. Cl.
CPC .. *A45D 26/0004* (2013.01); *A61B 17/320068* (2013.01); *A61B 17/54* (2013.01);
(Continued)

(58) Field of Classification Search
CPC ............ A61B 50/30; A61B 2050/3008; A61B 2017/00761; A45D 26/00; B26B 5/00;
(Continued)

(56) References Cited

U.S. PATENT DOCUMENTS 1,139,796 A 5/1915 Parker
2,457,772 A 12/1948 Milford et al.
(Continued)

FOREIGN PATENT DOCUMENTS

CN 2471294 Y 1/2002
CN 1758881 A 4/2006
(Continued)

OTHER PUBLICATIONS

Extended European Search Report for European Application No. 25173957.9 dated Sep. 24, 2025.
(Continued)

*Primary Examiner* — Anh T Dang

(74) *Attorney, Agent, or Firm* — Wolf, Greenfield & Sacks, P.C.

(57) ABSTRACT

A method and a hand-held device for dermaplaning is disclosed that includes a blade assembly which includes a blade, a blade holder and a safety cage. In accordance with an important aspect of the invention, the safety cage limits the amount of penetration of the blade into the facial skin to enable the device to be safely used by non-professionals. The dermaplaning device includes a vibration generator that causes the blade to vibrate at a predetermined frequency. Various embodiments of the hand-held dermaplaning device are disclosed for vibrating the blade.

9 Claims, 30 Drawing Sheets

Related U.S. Application Data continuation of application No. 17/021,690, filed on Sep. 15, 2020, now Pat. No. 10,993,519, which is a continuation of application No. 15/868,756, filed on Jan. 11, 2018, now Pat. No. 10,842,521, which is a continuation of application No. 14/976,409, filed on Dec. 21, 2015, now Pat. No. 10,441,307, which is a continuation-in-part of application No. 14/742,881, filed on Jun. 18, 2015, now Pat. No. 9,877,741, which is a continuation-in-part of application No. PCT/US2013/058708, filed on Sep. 9, 2013.

(51) Int. Cl.

| | |
|---|---|
| ***A61B 17/32*** | (2006.01) |
| ***A61B 17/54*** | (2006.01) |
| ***A61B 50/20*** | (2016.01) |
| ***A61H 23/02*** | (2006.01) |
| ***B26B 7/00*** | (2006.01) |
| ***H02J 7/00*** | (2006.01) |
| ***H02J 7/70*** | (2026.01) |
| ***H02J 50/10*** | (2016.01) |
| *A61B 17/00* | (2006.01) |

(52) U.S. Cl.

CPC ................ *A61B 50/20* (2016.02); *B26B 7/00* (2013.01); *H02J 7/00* (2013.01); *H02J 7/70* (2026.01); *H02J 50/10* (2016.02); *A45D 2200/1054* (2013.01); *A45D 2200/207* (2013.01); *A61B 2017/00398* (2013.01); *A61B 2017/00473* (2013.01); *A61B 2017/00734* (2013.01); *A61B 2017/00761* (2013.01); *A61B 2017/320071* (2017.08)

(58) Field of Classification Search

CPC ......... B26B 5/001; B26B 5/002; B26B 5/003; B26B 5/005; B26B 5/006; B26B 5/007; B26B 5/008; B26B 19/00; B26B 19/38; B26B 19/3806; B26B 19/3813

See application file for complete search history.

(56) References Cited

U.S. PATENT DOCUMENTS

| | | | |
|---|---|---|---|
| 3,509,626 | A | 5/1970 | Mead |
| 3,636,627 | A | 1/1972 | Tiffin |
| 3,650,029 | A | 3/1972 | Trelc |
| 3,749,092 | A | 7/1973 | Williams |
| 3,785,051 | A | 1/1974 | Dawidowicz et al. |
| 3,797,657 | A | 3/1974 | Petrillo |
| 3,835,532 | A | 9/1974 | Petrillo |
| 3,967,143 | A | 6/1976 | Watanabe et al. |
| 4,026,016 | A | 5/1977 | Nissen |
| 4,037,322 | A | 7/1977 | Bresler |
| 4,106,620 | A | 8/1978 | Brimmer et al. |
| 4,146,958 | A | 4/1979 | Chen et al. |
| 4,173,285 | A | 11/1979 | Kiraly et al. |
| 4,335,508 | A | 6/1982 | Francis et al. |
| 4,709,476 | A | 12/1987 | Shurtleff et al. |
| 4,739,553 | A | 4/1988 | Lazarchik |
| 4,741,103 | A | 5/1988 | Hultman |
| 4,928,716 | A | 5/1990 | Greene |
| 5,016,352 | A | 5/1991 | Metcalf |
| 5,026,387 | A | 6/1991 | Thomas |
| 5,095,619 | A | 3/1992 | Davis et al. |
| 5,113,585 | A | 5/1992 | Rogers et al. |
| 5,191,712 | A | 3/1993 | Crook et al. |
| 5,207,696 | A | 5/1993 | Matwijcow |
| 5,220,728 | A | 6/1993 | Ueno et al. |
| 5,249,361 | A | 10/1993 | Apprille, Jr. et al. |
| 5,299,354 | A | 4/1994 | Metcalf et al. |
| 5,324,299 | A | 6/1994 | Davison et al. |
| 5,410,810 | A | 5/1995 | Gillibrand |
| D361,866 | S | 8/1995 | Febus |
| 5,518,114 | A | 5/1996 | Kohring et al. |
| 5,702,351 | A | 12/1997 | Bar-Or et al. |
| 5,931,859 | A | 8/1999 | Burke |
| 5,934,291 | A | 8/1999 | Andrews |
| 6,119,035 | A | 9/2000 | Wang |
| 6,119,038 | A | 9/2000 | Cook |
| 6,164,290 | A | 12/2000 | Andrews |
| 6,224,565 | B1 | 5/2001 | Cimino |
| 6,629,983 | B1 | 10/2003 | Ignon |
| D531,754 | S | 11/2006 | Lee |
| D532,157 | S | 11/2006 | Lee |
| 7,384,405 | B2 | 6/2008 | Rhoades |
| 7,761,998 | B2 | 7/2010 | Blaustein et al. |
| 8,052,662 | B2 | 11/2011 | Zelickson et al. |
| 8,132,332 | B2 | 3/2012 | Tautscher et al. |
| 8,745,876 | B2 | 6/2014 | Hage et al. |
| 9,265,516 | B2 | 2/2016 | Casey et al. |
| 9,877,741 | B2 | 1/2018 | Levy |
| 9,918,539 | B2 | 3/2018 | Levy |
| 10,111,681 | B2 | 10/2018 | Levy |
| 10,363,059 | B2 | 7/2019 | Levy |
| 10,441,307 | B2 | 10/2019 | Levy |
| 10,485,559 | B2 | 11/2019 | del Rio et al. |
| 10,842,521 | B2 | 11/2020 | Levy |
| 10,993,519 | B2 | 5/2021 | Levy |
| 2002/0184770 | A1 | 12/2002 | Peyser |
| 2003/0233085 | A1 | 12/2003 | Giammarusti |
| 2004/0172831 | A1 | 9/2004 | Paas et al. |
| 2004/0185067 | A1 | 9/2004 | Daikuzono |
| 2004/0225309 | A1 | 11/2004 | Eriksson et al. |
| 2005/0043653 | A1 | 2/2005 | Trimmer et al. |
| 2005/0234477 | A1 | 10/2005 | Brown et al. |
| 2006/0032053 | A1 | 2/2006 | Saker |
| 2006/0122631 | A1 | 6/2006 | Kertz |
| 2006/0143926 | A1 | 7/2006 | Khubani et al. |
| 2007/0050982 | A1 | 3/2007 | Freund et al. |
| 2007/0154419 | A1 | 7/2007 | Hattendorf et al. |
| 2007/0293795 | A1 | 12/2007 | Carroll |
| 2008/0139974 | A1 | 6/2008 | Da Silva |
| 2009/0048557 | A1 | 2/2009 | Yeshurun et al. |
| 2009/0071008 | A1 | 3/2009 | Hart et al. |
| 2009/0124985 | A1 | 5/2009 | Hasenoehrl et al. |
| 2009/0138027 | A1 | 5/2009 | Lucas et al. |
| 2009/0202654 | A1 | 8/2009 | Nixon |
| 2009/0235529 | A1 | 9/2009 | Ringart et al. |
| 2009/0270684 | A1 | 10/2009 | Nielsen et al. |
| 2009/0275864 | A1 | 11/2009 | Hirai |
| 2010/0168741 | A1 | 7/2010 | Sanai et al. |
| 2010/0228182 | A1 | 9/2010 | Clark, III et al. |
| 2010/0299928 | A1 | 12/2010 | Clarke et al. |
| 2011/0196405 | A1 | 8/2011 | Dietz |
| 2012/0101512 | A1 | 4/2012 | Locke et al. |
| 2013/0073001 | A1 | 3/2013 | Campbell |
| 2013/0144280 | A1 | 6/2013 | Eckhouse et al. |
| 2015/0073438 | A1 | 3/2015 | Levy |
| 2016/0166273 | A1 | 6/2016 | Levy |
| 2017/0042568 | A1 | 2/2017 | Levy |
| 2017/0265629 | A1 | 9/2017 | Levy |
| 2018/0125524 | A1 | 5/2018 | Levy |
| 2018/0206880 | A1 | 7/2018 | Levy |
| 2018/0256192 | A1 | 9/2018 | Levy |
| 2020/0405342 | A1 | 12/2020 | Levy |
| 2021/0274907 | A1 | 9/2021 | Levy |

FOREIGN PATENT DOCUMENTS

| | | | |
|---|---|---|---|
| CN | 201051937 | Y | 4/2008 |
| CN | 201070768 | Y | 6/2008 |
| CN | 101612045 | A | 12/2009 |
| CN | 101790443 | A | 7/2010 |
| CN | 102639302 | A | 8/2012 |
| CN | 102655816 | A | 9/2012 |
| CN | 102871706 | A | 1/2013 |
| CN | 202723939 | U | 2/2013 |
| CN | 203447382 | U | 2/2014 |
| CN | 103747745 | A | 4/2014 |
| DE | 9312913 | U1 | 10/1993 |

(56) References Cited

FOREIGN PATENT DOCUMENTS

| | | | |
|---|---|---|---|
| EP | 0 387 176 | A1 | 9/1990 |
| EP | 0 451 381 | A1 | 10/1991 |
| EP | 1 972 417 | A1 | 9/2008 |
| EP | 3 117 736 | A1 | 1/2017 |
| FR | 2811524 | A1 | 1/2002 |
| GB | 2 398 533 | A | 8/2004 |
| JP | 2000-060927 | A | 2/2000 |
| JP | 2001-245400 | A | 9/2001 |
| JP | 2003-103074 | A | 4/2003 |
| JP | 2003-126204 | A | 5/2003 |
| JP | 2005-270120 | A | 10/2005 |
| JP | 2009-279293 | A | 12/2009 |
| KR | 10-2004-0022550 | A | 3/2004 |
| KR | 10-2008-0006875 | A | 1/2008 |
| RU | 2320476 | C2 | 3/2008 |
| WO | WO 97/37819 | A2 | 10/1997 |
| WO | WO 00/19854 | A1 | 4/2000 |
| WO | WO 03/101243 | A1 | 12/2003 |
| WO | WO 2005/002386 | A1 | 1/2005 |
| WO | WO 2006/098248 | A1 | 9/2006 |
| WO | WO 2015/034530 | A1 | 3/2015 |
| WO | WO 2015/094615 | A1 | 6/2015 |
| WO | WO 2017/112652 | A1 | 6/2017 |

OTHER PUBLICATIONS

Chinese Office Action dated May 10, 2024, in connection with Chinese Application No. 20221279324.8, and English translation thereof.

International Search Report and Written Opinion for International Application No. PCT/US2013/058708, mailed Feb. 11, 2014.

International Preliminary Report on Patentability for International Application No. PCT/US2013/058708, mailed Mar. 24, 2016.

Extended European Search Report for European Application No. 13893037.5, dated Mar. 9, 2017.

International Search Report and Written Opinion for International Application No. PCT/US2016/067738, mailed May 18, 2017 (D0803.70009WO00).

Extended European Search Report for European Application No. 16879960.9, dated Aug. 22, 2019 (D0803.70009EP00).

Extended European Search Report for European Application No. 21204709.6, dated Mar. 22, 2022 (D0803.70009EP01).

First Third-Party Submission for U.S. Appl. No. 14/976,409, filed Oct. 13, 2017 (D0803.70009US00).

Second Third-Party Submission for U.S. Appl. No. 14/976,409, filed Oct. 13, 2017.

[No Author Listed] bt-Micro™—Demonstration Video. http:/www.youtube.com/watch?v=W1PcSf253cs [dated Jul. 15, 2012].

[No Author Listed] Features of Japanese Bi-Hada Sonic Body Beautifying Razor, 2 pages [date unknown].

[No Author Listed] How the Dermasonic Wand Works. http:/dermasonic.com/how.html [available prior to Oct. 30, 2013].

[No Author Listed] http:/www.youtube.com/watch?NR=1&v=jypKlrpGD1g&feature=fvwp [available prior to Oct. 30, 2013].

[No Author Listed] Kai Bi-hada Ompa Product Listing. Cosme. http://us.cosme.net/products/show/10040006, 2 pages. Release date Apr. 1, 2012.

[No Author Listed] Package Label for Ompa Bi-Hada Razor with Sonic-Wave Oscillation Technology. Kai Razor, 3 pages [date unknown].

[No Author Listed] Picture of L-Type Sonic-Wave Oscillation Razor, 2 pages [date unknown].

[No Author Listed] Screen captures from YouTube video clip entitled "[貝印][カミソリ] bi-hada うぶげケアのおはなし",published on Nov. 4, 2011, by user "MovieContents 貝印" at https://www. youtube.com/watch?v=93uvJO-FilA, 3 pages.

[No Author Listed] Screen captures from YouTube Video clip entitled "Incredible Anti Aging Secret Using a Razor also called Derma Planing. skin shaving.", published on Feb. 23, 2012 by user "Morganna Lefay" at https://www.youtube.com/watch?v=07461QJ9hSI, 9 pages.

[No Author Listed] Skin Scrubber—Cosmo C&T Korea (Sonic Peeler). http:/www.youtube.com/watch?v=fmSS2uexmac [dated May 3, 2011].

Lam, The Awesome Tinkle Eyebrow Razors. "mymakeupblog" Webpage. mymakeupblog.blogspot.com/2011/OS/awesome-tinkle-eyebrow-razors.html, May 11, 2011, 6 pages.

Sonoko, Yajima mini review Kai "bi-hada ompa holder". Impress Corporation. https://kaden.watch.impress.co.jp/docs/column_review/yajreview/541145.html. Jun. 21, 2012, 16 pages.

| index | part name | material | qty | index | part name | material | qty | index | part name | material | qty | index | part name | material | qty | index | part name | material | qty |
|---|---|---|---|---|---|---|---|---|---|---|---|---|---|---|---|---|---|---|---|
| 401 | Top housing | ABS | 1 | 410 | Sensor soft bumper | NBR | 2 | 419 | Charger base cover | ABS | 1 | 428 | Steel for charger | Steel | 1 | 437 | Blade asem | ABS+SUS | 8 |
| 402 | Middle main bracket | PC | 1 | 411 | Blade sensor a | PC & POM | 1 | 420 | Rubber foot | NBR | 4 | 429 | Charger PCB | / | 4 | | | | |
| 403 | Battery (Li-ion) | Li-ion | 1 | 412 | Rubber seal cover | POM | 1 | 421 | Ballast block | Steel | 1 | 430 | Base housing | ABS | 1 | | | | |
| 404 | Magnet | Magnet | 1 | 413 | Vibrator motor | / | 1 | 422 | Cutter | POM | 1 | 431 | DC jack socket | / | 1 | | | | |
| 405 | Main PCB | / | 1 | 414 | Blade sensor b | PC & POM | 1 | 423 | Cutter spring | SUS | 1 | 432 | Screw cover | ABS | 1 | | | | |
| 406 | Switch button bracket | PC | 1 | 415 | Blade sensor seal ring | Si-rubber | 2 | 424 | Fastener spring | SUS | 1 | 433 | Transmitter coil holder | ABS | 1 | | | | |
| 407 | Silicon rubber button | Si-rubber | 1 | 416 | Bottom seal rubber | TPE | 1 | 425 | Blade lock | POM | 1 | 434 | Transmitter coil | / | 1 | | | | |
| 408 | Main dect switch | / | 1 | 417 | Blade sensor bracket | POM | 1 | 426 | Foam bumper for steel | NBR | 1 | 435 | Receive coil | / | 1 | | | | |
| 409 | Sensor dect switch | / | 2 | 418 | Charger base top | ABS | 1 | 427 | Magnet switch | / | 1 | 436 | Blade cartridge | PC | 1 | | | | |

*Fig. 27b*

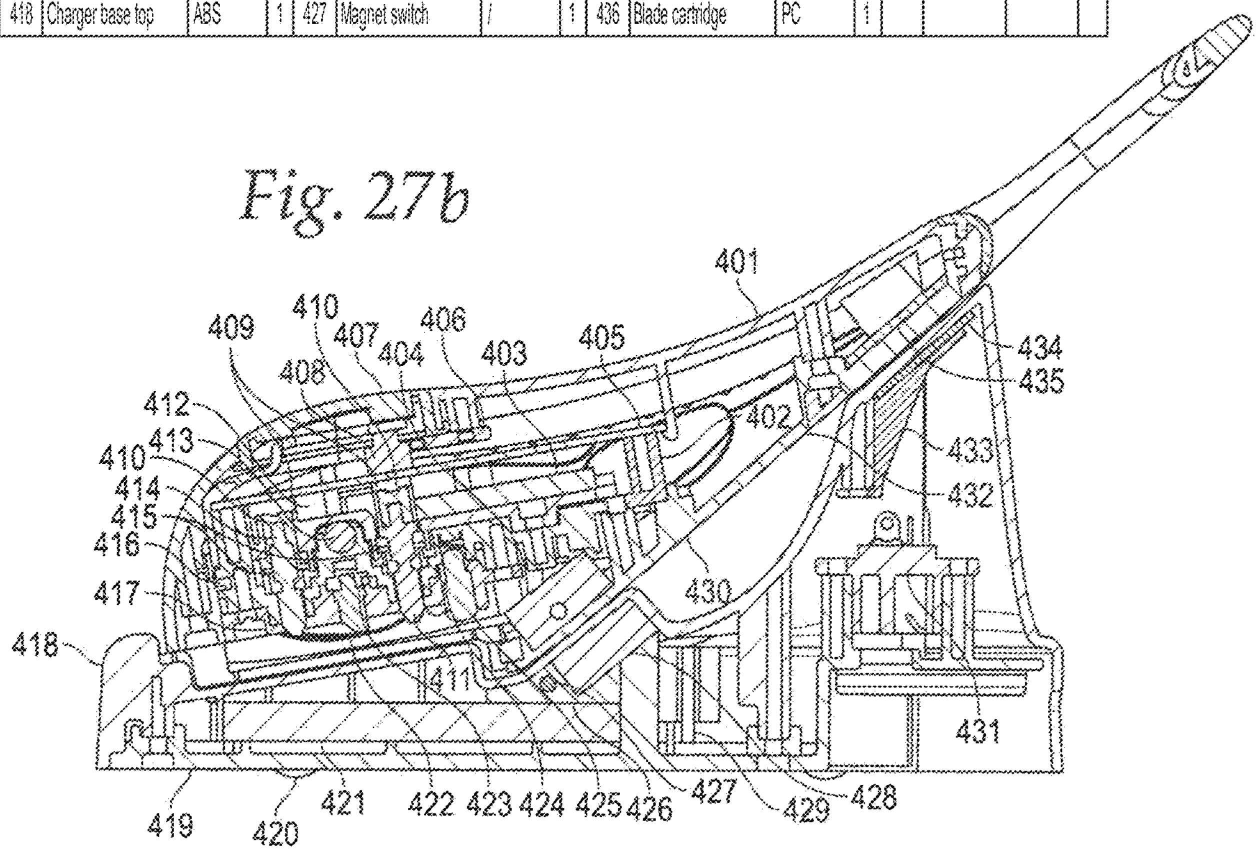

HAND HELD DERMAPLANING DEVICE AND DERMAPLANING PROCESS

RELATED APPLICATIONS

This application is a division of U.S. application Ser. No. 17/198,446, filed Mar. 11, 2021, which is a continuation of U.S. application Ser. No. 17/021,690, filed Sep. 15, 2020, now U.S. Pat. No. 10,993,519, which is a continuation of U.S. application Ser. No. 15/868,756, filed Jan. 11, 2018, now U.S. Pat. No. 10,842,521, which is a continuation of U.S. application Ser. No. 14/976,409, filed on Dec. 21, 2015, now U.S. Pat. No. 10,441,307, which is a continuation-in-part of U.S. application Ser. No. 14/742,881, filed on Jun. 18, 2015, now U.S. Pat. No. 9,877,741, which is a continuation-in-part of International Application No. PCT/US2013/058708, filed on Sep. 9, 2013, which are herein incorporated by reference in their entirety.

BACKGROUND OF THE INVENTION

1. Field of the Invention

The present invention relates to hand held device and process used in treating facial skin and more particularly to a hand held dermaplaning device for exfoliating facial skin that is safe to use by non-professionals as well as a process for dermaplaning facial skin.

2. Description of the Prior Art

Various processes are known for treating facial skin. These processes are known to include hand-held devices and fall into several categories as follows:

Shaving
Cleansing and Moisturizing
Dermabrasion
Dermaplaning (Exfoliation)
Debridement Shaving is used to remove facial hair by way of a razor. In addition to standard safety razors, U.S. Pat. No. 3,509,626 and Russian Patent RU 2320476 disclose safety razors with piezo-electric crystals attached to the blade for vibrating the blade at ultrasonic frequencies during shaving. These devices include a safety razor, a piezo-electric crystal, battery and a circuit for coupling the battery to the piezo-electric crystal. These devices are used for removing excess hair from a person's face and do not remove any skin. Such devices are configured for non-professional use.

In addition to manual treatment, cleansing and moisturizing may be accomplished by way of hand-held devices. For example, US Patent Application Publication No. US 2005/0043653 A1 and U.S. Pat. Nos. 5,931,859 and 6,119,035 disclose hand held devices for dispensing a liquid to a person's face. These devices include a cleansing mode in which a micro-current is applied to cleanse the skin. US Patent Application Publication No. US 2008/0139974 A1 discloses a hand held device for just applying a moisturizing liquid to a person's face. An example of such a device is also disclosed in: http:/www.youtube.com/watch?v=WlPcSf253cs.

Other hand-held devices are known for cleansing facial skin which rely on ultrasonic frequencies. Examples of these devices are disclosed in Japanese Patent No. JP20000060427; South Korean Patent Nos.: KR 20040022550 and KR 20080006875. Additional examples of such devices can be found at the following locations: http:/youtube.com/watch?NR=1&v=jypKIrpGDIg&feature=fvwp; http:/youtube.com/watch?v=fmSS2uexmac and http:/dermasonic.com/how.html. Such devices are also configured for non-professional use.

Dermabrasion is a cosmetic surgical procedure for removing an outer layer of skin by abrading the skin with fine sandpaper or wire brushes to remove scars or other imperfections. This procedure is used to abrade the skin down to the dermis. The dermis is a layer of skin between the epidermis and subcutaneous tissues that consist of connective tissue and cushions the body from stress and strain. Dermabrasion normally requires an anesthetic and is normally done by medical professionals, such as dermatologists. Because of the possibility of infections and scarring, dermabrasion is a relatively unpopular choice for facial skin treatment.

Hand held devices for performing dermabrasion are known. Exemplary hand-held devices used for dermabrasion are disclosed and described in detail in U.S. Pat. No. 8,052,662 and US Patent Application Publication Nos. US 2003/0233085 A1; US 2004/0185067 A1; US 2007/0293795 A1; US 2009/0048557 A1; US 2009/0124985 A1; and US 2013/0144280 A1. In general, such devices include an applicator having an abrasive material applied to the surface. The applicator is attached to a piezo-electric crystal for vibrating the applicator at ultrasonic frequencies. The vibrating applicator is applied to areas of the face of interest. U.S. Pat. No. 7,384,405 discloses a hand-held device that includes a rotating brush with abrasive bristles. Hand-held dermabrasion devices are known to be available for professional and non-professional use.

Debridement is a surgical technique performed by a licensed physician for removing unhealthy tissue, such as, necrotic, i.e., dead, infected, damaged, contaminated tissue or in situations to remove a foreign body in the tissue. US Patent Application Publication No. US 2012/0101512 A1 discloses a hand held device that is known to be used for debridement. The device includes blade carried by a handle. The blade is a small, dull flat blade operable to scrape the necrotic tissue away from the tissue site without harming any of the healthy tissue located adjacent the necrotic tissue. A piezoelectric crystal is attached to the blade to vibrate the blade at ultrasonic frequencies. Such debridement devices are only available for professional use.

Dermaplaning is a relatively popular process that is relatively simple and safe and is used for exfoliating the epidermis, i.e. outer layer of cells in the skin, and removing fine vellus hair, i.e. peach fuzz, from the skin. Dermaplaning is a process normally performed by licensed skin care professionals, such as, estheticians, because of the use of a scalpel or similar blade. Using a scalpel and a delicate touch, the scalpel is swept across the skin with light feathering strokes to exfoliate the skin. Exfoliation involves the removal of the oldest dead skin cells on the skin's outermost surface.

Dermaplaning facial skin has many benefits. For example, removing epidermal skin allows skin care products to penetrate more readily into deeper layers of the skin for better results. As mentioned above, dermaplaning removes vellus hair which tends to cause a build-up of dirt and oils in the follicles. Removal of the hair results in healthier looking skin.

Hand-held devices used for dermaplaning normally include a surgical style scalpel consisting of a blade and a handle. Such scalpels are not available for non-professional use. As such, dermaplaning is only available at spas with licensed skin care professionals. Such dermaplaning treatments at spas can be relatively expensive. Unfortunately, there are no known dermaplaning devices known for non-professional home use. Thus, there is a need to provide a hand-held device and method for dermaplaning for non-professional use that overcomes this problem.

SUMMARY OF THE INVENTION

Briefly, the present invention relates a method and a hand-held device for dermaplaning facial skin that is relatively safe for non-professional use. The hand-held device includes a blade assembly that includes a blade, a blade holder and a safety cage that is removably mounted to a housing. The safety cage limits the depth that the blade can penetrate the skin which makes the device safe for use by non-professionals. Various embodiments of the hand-held dermaplaning device are contemplated. In one embodiment, a piezoelectric crystal is used to cause the blade to vibrate at ultrasonic frequencies. In an alternate embodiment, a motor driving an eccentric load may be used for vibrating the blade assembly at other frequencies. In yet another embodiment, the motor with an eccentric load and the piezoelectric crystal are selectively and alternatively used to vibrate the blade assembly. In embodiments that include a motor, the motor speed may be optionally adjustable to enable the vibration frequency to be varied. A dermaplaning process is also disclosed that can be used by non-professionals.

BRIEF DESCRIPTION OF DRAWINGS

These and other advantages of the present invention will be readily understood with reference to the following specification and attached drawing wherein:

FIG. 4B illustrates a position in ultrasonic mode; FIG. 4C illustrates an intermediate OFF position and FIG. 4D illustrates a sonic mode.

FIG. 27*b* is a more detailed elevational view of the dermaplaning device illustrated in FIG. 21, shown with the housing removed and mounted in the portable stand illustrated in FIG. 25*b*, shown with a table of component parts keyed to reference numbers in circles.

DETAILED DESCRIPTION

The present disclosure includes a method and a hand-held device for dermaplaning that is relatively safe for non-professional use. In general, the hand-held device includes a blade assembly removably mounted to a housing. The blade assembly includes a blade or scalpel, a blade holder for carrying the blade and a safety cage. The safety cage is juxtaposed or disposed over the cutting edge of the blade which limits the amount of penetration of the blade into the facial skin. As such, use of the device enables non-professionals to safely perform dermaplaning on a person's face.

Multiple exemplary embodiments of the dermaplaning device are described and illustrated. All embodiments include an exemplary outer housing, for example, as illustrated in FIGS. 1-18 and 21-23 and a blade assembly and a vibration generator, The first embodiment, illustrated in FIGS. 1-6, includes a piezoelectric crystal circuit for vibrating the blade at an ultrasonic frequency, for example, frequencies above 20,000 Hertz and a motor with an eccentric rotary load which vibrates the blade assembly at frequencies other than ultrasonic frequencies, for example, frequencies less than 20,000 Hertz.

The second embodiment is illustrated in FIGS. 7-11. In this embodiment, the dermaplaning device only includes a piezoelectric crystal circuit attached to the blade.

The third embodiment is illustrated in FIGS. 12, 13, 13A, 13G, 14 and 15. In this embodiment, the dermaplaning device a motor with a rotary eccentric load as a vibration generator.

Figure 35:
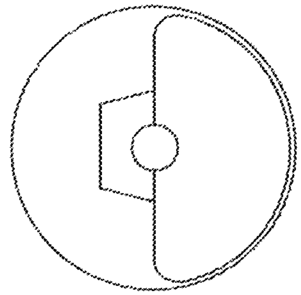
FIG. 35 is a front elevational view of an exemplary vibration generator, illustrated in FIG. 34.

A fourth exemplary embodiment is illustrated in FIGS. 21-23, 24A, 24B, 27A, 27B and 32-37. This embodiment includes a vibration generator, for example, a motor and an eccentrically mounted mass mounted on the motor shaft, as illustrated in FIGS. 34 and 35.

Figure 23:
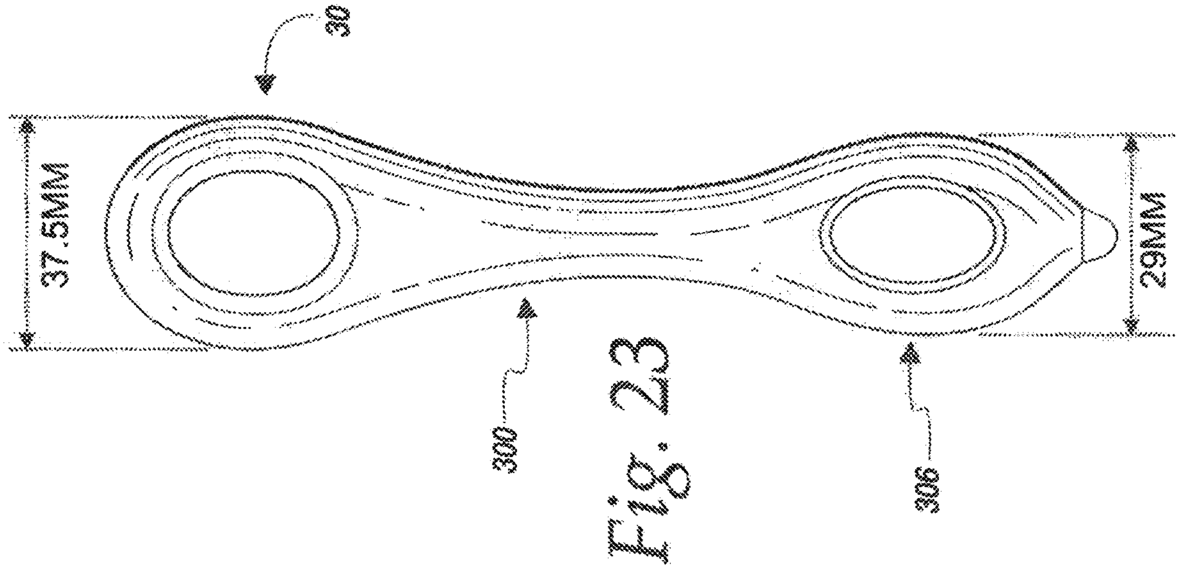
FIG. 23 is a top view of the dermaplaning device illustrated in FIG. 21, also shown with exemplary dimensions.
Figure 24A:
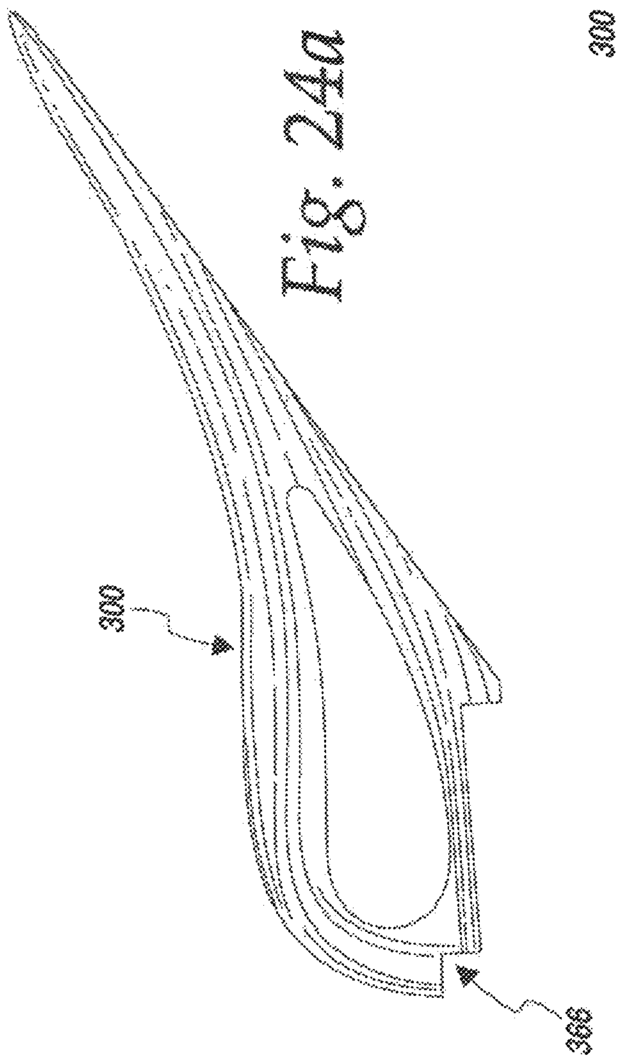
FIG. 24*a* is a side elevational view of the dermaplaning device illustrated in FIGS. 21-23 shown with the blade assembly removed.
Figure 24B:
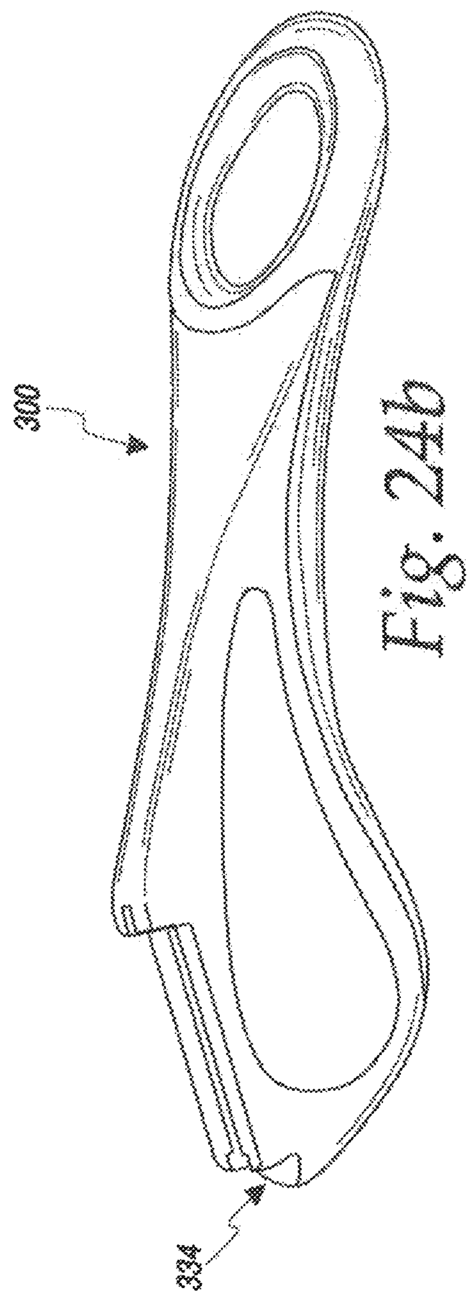
FIG. 24*b* is similar to FIG. 24*a* shown with the dermaplaning device upside down to illustrate the guide rails on the dermaplaning device for slidably receiving a blade assembly.
Figure 25B:
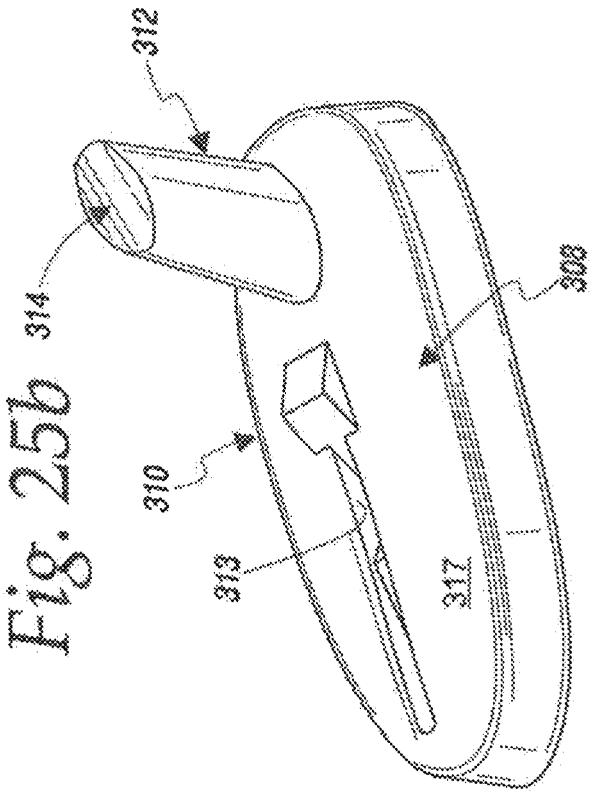
FIG. 25*b* is an isometric view of the portable stand illustrated in FIG. 25*a*.
Figure 25A:
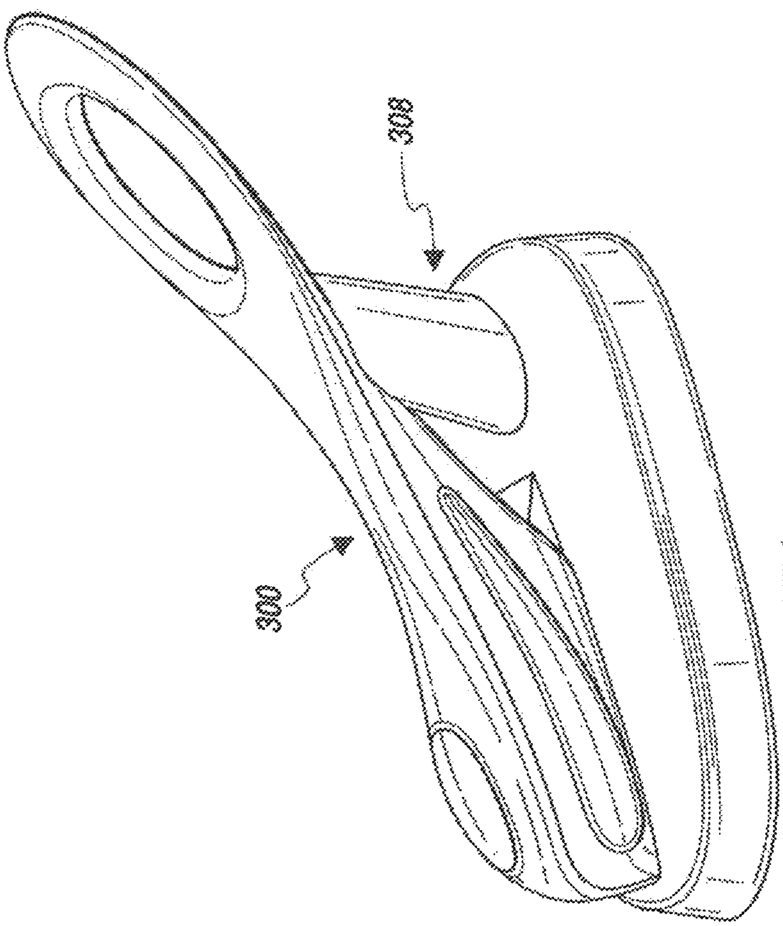
FIG. 25*a* is an isometric view of the dermaplaning device illustrated in FIG. 21 shown carried by an exemplary portable stand.
Figure 26:
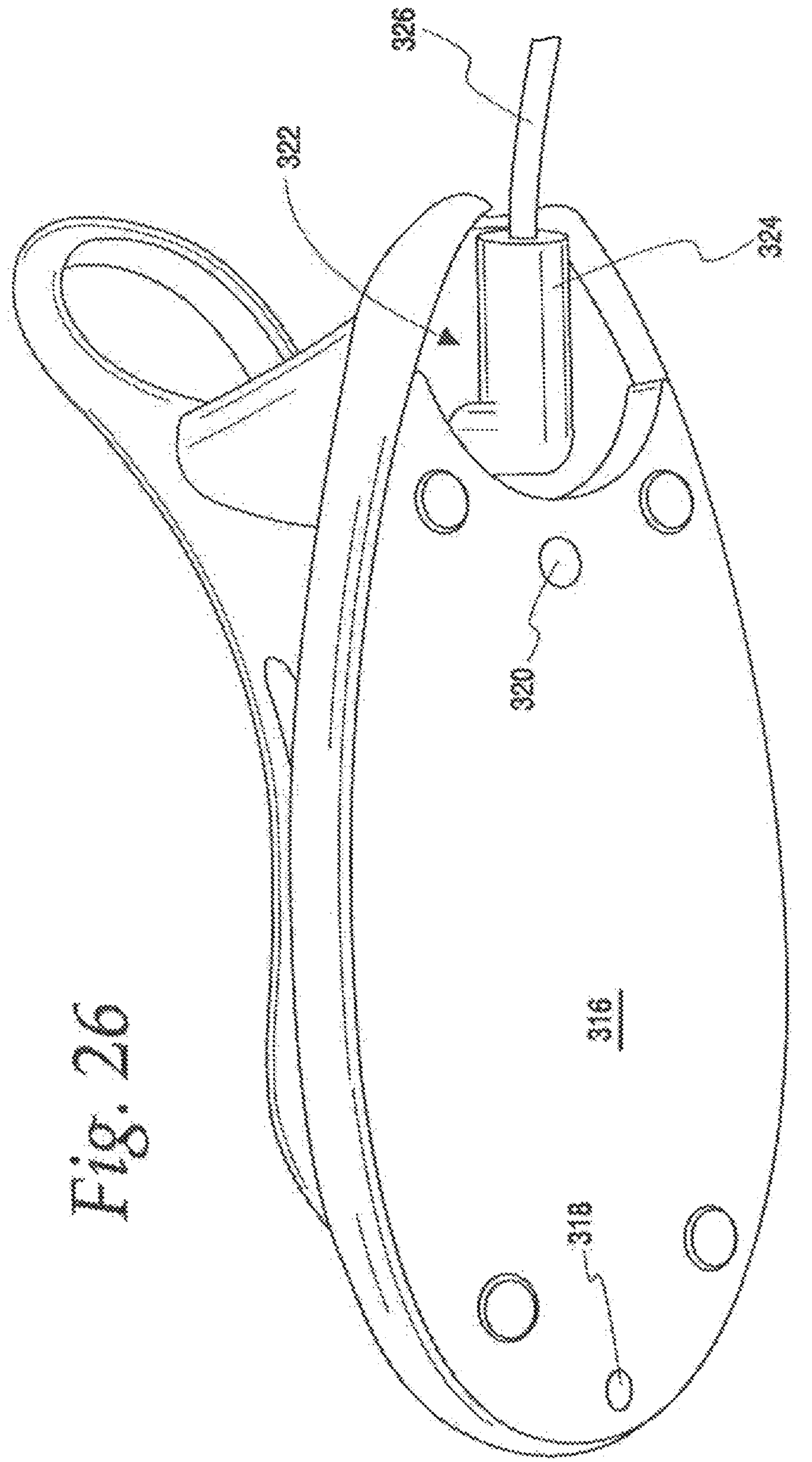
FIG. 26 is an isometric view of the dermaplaning device and portable stand illustrated in FIG. 25*b*, shown tipped on its side to illustrate the bottom of the portable stand and the power connection.
Figure 27A:
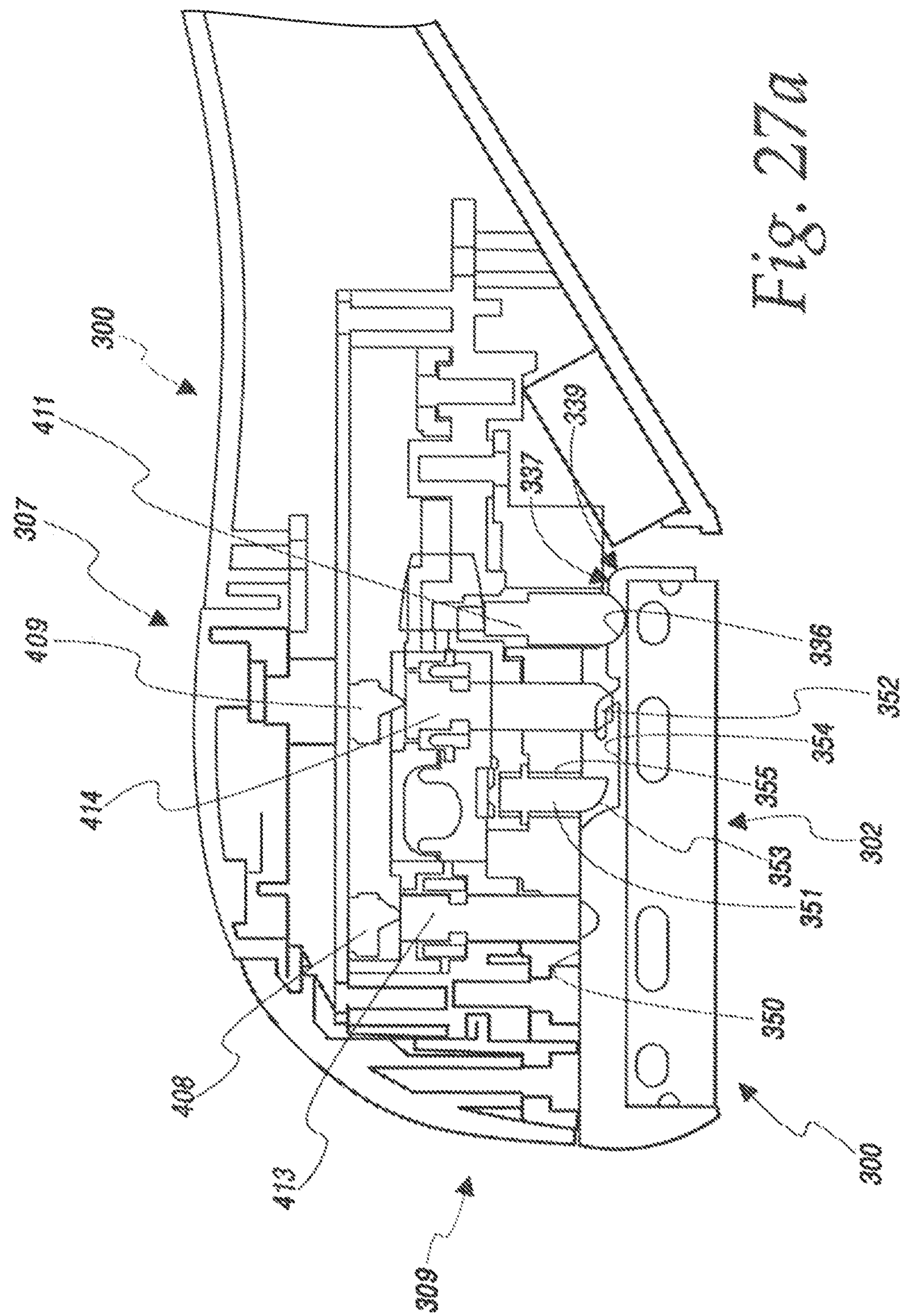
FIG. 27*a* illustrates an enlarged partial sectional view of the dermaplaning device illustrated in FIG. 21 shown with a blade inserted and the housing removed.
Figure 29:
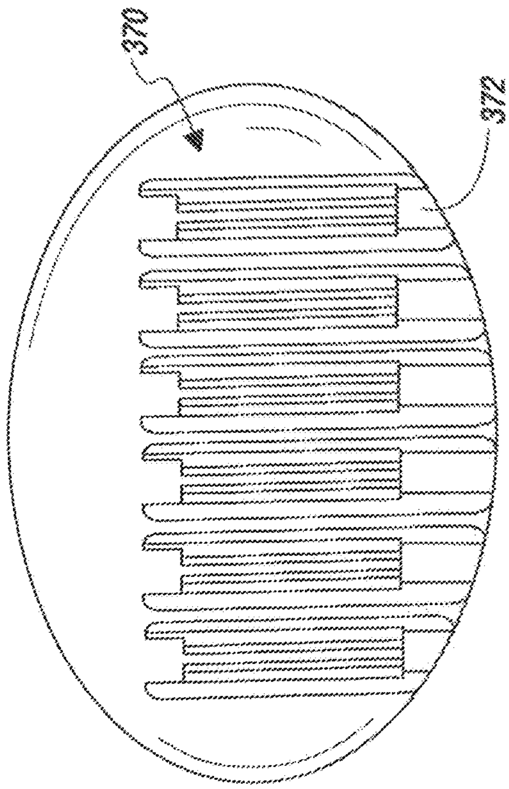
FIG. 29 is a top view of an exemplary blade retainer for use in storing additional blade assemblies as illustrated in FIG. 28.
Figure 28:
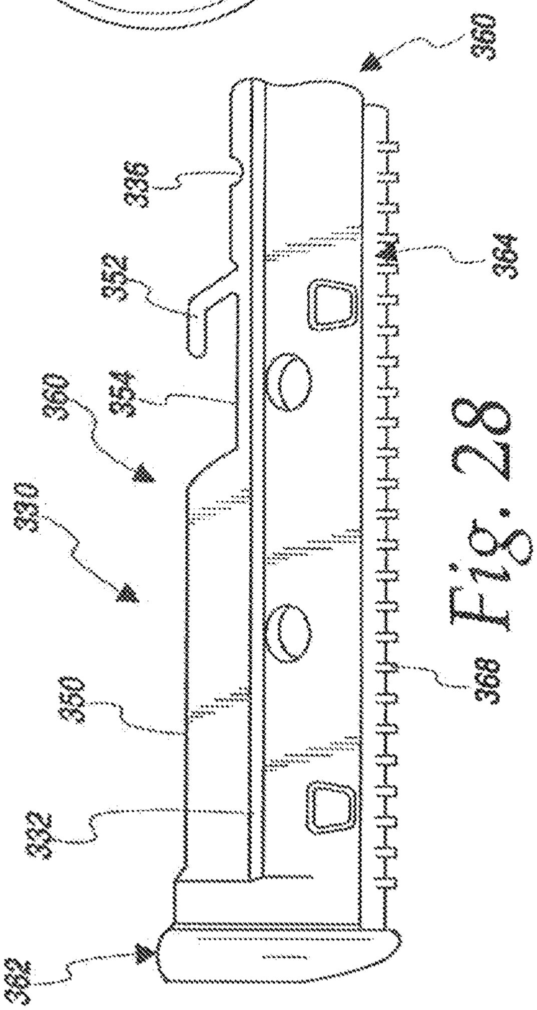
FIG. 28 illustrates an exemplary blade assembly shown which include a blade, a blade holder and a safety cage.
Figure 30:
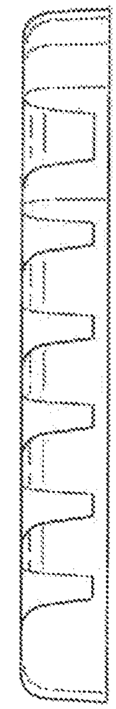
FIG. 30 is a front elevational view of the blade retainer illustrated in FIG. 29.
Figure 31:
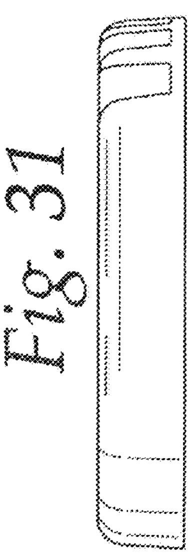
FIG. 31 is a side elevational view of the blade retainer illustrated in FIG. 29.
Figure 41:
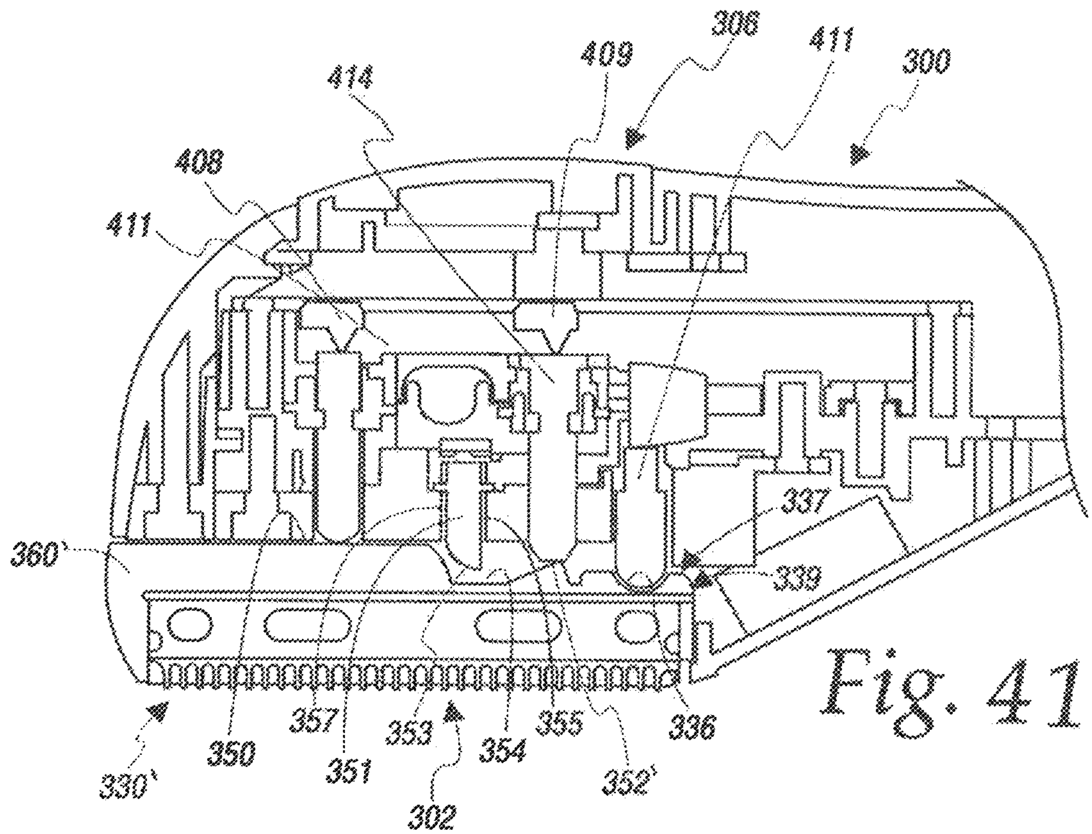
FIG. 41 is a partial elevational view of a dermaplaning device as illustrated in FIGS. 21-23 with an alternative embodiment of the blade assembly fully loaded with the housing removed illustrating the relationship between the alternative embodiment of the blade assembly and the blade control mechanism.
Figure 42:
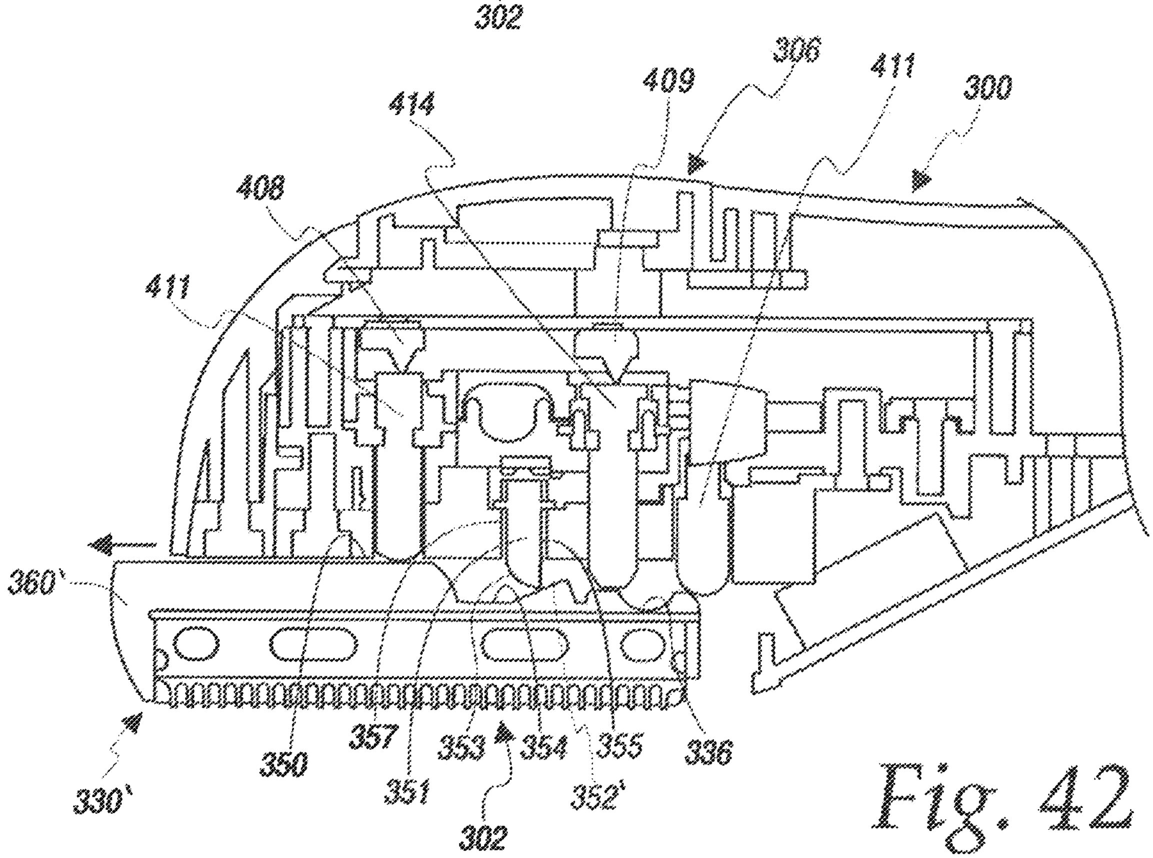
FIG. 42 is similar to FIG. 41 but shown with the alternative blade assembly removed.

FIGS. 25A, 25B and 26 illustrate an exemplary base tor the device illustrated in FIGS. 21-23, 24A, 24B, 27A, 27B 36-38, 41 and 42. FIG. 28 illustrates an exemplary blade assembly for the fourth embodiment. FIGS. 41 and 42 illustrate an exemplary alternative embodiment of the blade assembly illustrated in FIG. 28. FIGS. 29-31 illustrate an exemplary blade retainer for the blade assemblies illustrated in FIGS. 28, 41 and 42.

Fourth Embodiment

Figure 21:
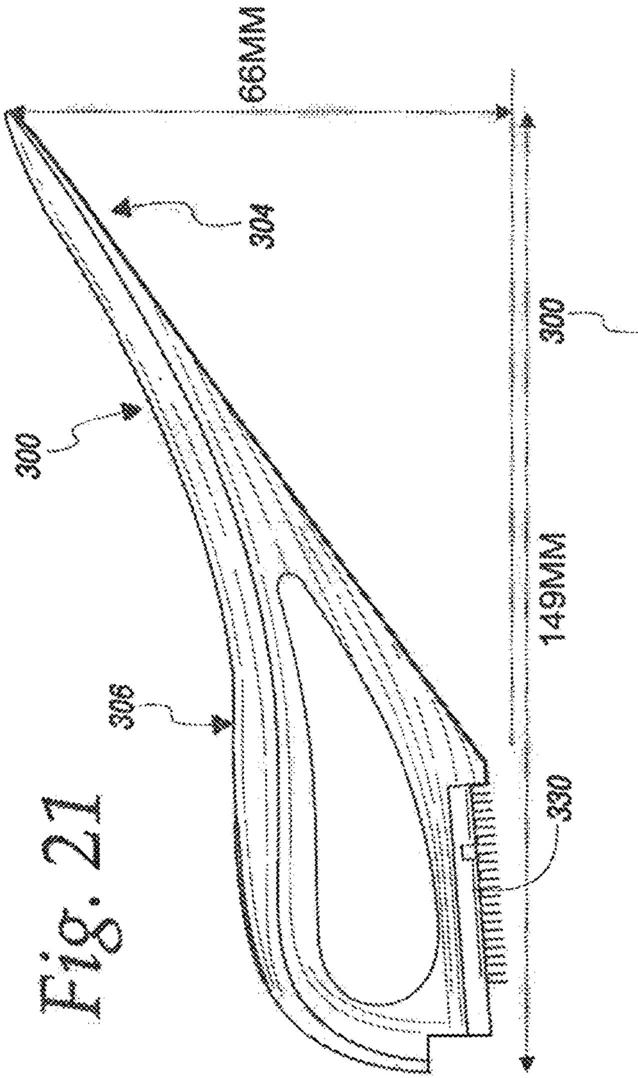
FIG. 21 is a side elevational view of an alternate exemplary embodiment of the exemplary dermaplaning device illustrated in FIG. 1, shown with exemplary dimensions and shown with a blade assembly installed.
Figure 22:
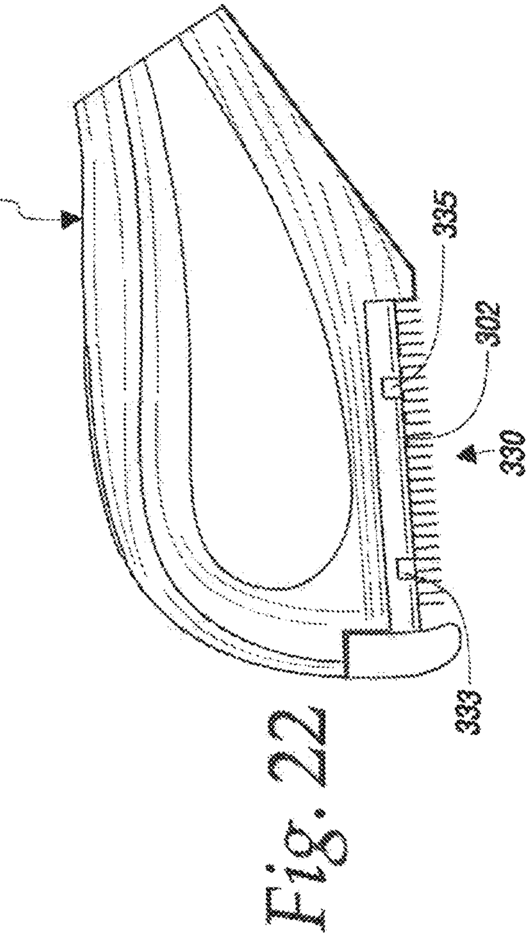
FIG. 22 is a partial enlarged view of the dermaplaning device illustrated in FIG. 21.

The fourth embodiment of the dermaplaning device is illustrated in FIGS. 21-23 and 36-42. Referring first to FIGS. 21-23, 24A, 24B and 24C, an exemplary housing for the fourth exemplary embodiment of the dermaplaning device is illustrated. An exemplary outline is shown. FIGS. 21-23 illustrate a housing the dermaplaning device with the blade assembly installed while FIGS. 24A and 24B illustrate the dermaplaning device with the blade removed. The housing can accommodate the blade assembly illustrated in FIG. 28 as well as the blade assembly illustrated in FIGS. 41 and 42 as well as any blade assembly which can be inserted and removed and satisfy the functional interlocks of the blade control mechanism, as discussed below. The dermaplaning device, identified with the reference numeral 300 (FIGS. 21-24B), includes a removable blade assembly 330, a handle portion 304 and a base portion 306 form an outer housing.

FIGS. 25A, 25B and 26 illustrate an exemplary base or stand for storing and charging the dermaplaning device 300. In the exemplary embodiment shown, the exemplary stand 310 is configured to receive a dermaplaning device without a blade assembly, such as the device shown in in FIGS. 24A and 24B. One of the reasons for configuring the stand 310 in this manner is that the blade assembly is to be removed after each use for sanitary reasons. As will be discussed in more detail below, a blade assembly control mechanism in the device is configured to break off an upwardly extending tab 352, for example, an L-shaped tab 352 or other upwardly extending tab that is configured so that the blade assembly can be fully inserted and broken off as the blade assembly is being removed. If an attempt is made to re-insert the blade assembly 330 after the tab is broken off, the blade assembly control mechanism 309 will sense the lack of the tab 352 and prevent the device from operating.

As best shown in FIG. 25B, the exemplary base 308 includes a cradle portion 310 for receiving the base portion 306 of the dermaplaning device 300 and a stand portion 312 to enable the handle portion 304 of the device 300 to rest upon it. As shown, the cradle portion 310 is formed with a slot 313 contoured to the bottom support surfaces of the base portion 306 of the dermaplaning device 300, as shown in FIGS. 24A and 24B. The slot 313 is contoured so that the base portion 306 of the dermaplaning device 300 rests upon the bottom surfaces of the slot 310 and the sidewalls of the base portion 306 of the dermaplaning device 300 are in contact with the sidewalls 313 of the slot 310.

The stand portion 312 is used to support the dermaplaning device 300 in an upright position at approximately at an angle of 50.degree. from the horizontal, as shown in FIG. 25A. A top surface 314 of the stand portion 312 is angled to support the handle portion 304 intermediate the free end.

In the exemplary embodiment shown, the connection between the dermaplaning device 300 and the base 308 is a mechanical connection. As will be discussed in more detail below, the exemplary device may also include an induction charger. The primary winding of the induction charger is carried in the base and "connects" by magnetic induction to a secondary winding and a battery charger in the device 300. In such an embodiment shown, the dermaplaning device 300 is formed as a portable device and may include an internal rechargeable battery. The induction type battery charger may be implemented for charging the internal battery. As will be discussed in more detail below, the internal battery is charged by induction when the dermaplaning device 300 is seated in the base 308. The components are configured so that the secondary of the induction battery charger is within a predetermined distance from the primary side of the induction battery charger. Thus, the internal battery is charged even though there is no electrical contact between the dermaplaning device 300 and the base 308.

Various alternate embodiments are also contemplated. One alternate embodiment contemplates an internal battery that is not re-chargeable. In such an embodiment, the non rechargeable battery is periodically replaced. In other alternate embodiments which include re-chargeable batteries, external electrical contacts are formed on the exterior of the dermaplaning device 300 that are configured to mate with corresponding contacts on the base 308. In this embodiment, the external contacts on the base 308 are connected to an external source of AC or DC for charging the internal rechargeable battery.

In yet another alternate embodiment, the dermaplaning device 300 is powered from an external source of AC that is hardwired into the device 300. This embodiment requires a constant source of AC power for operation.

In the embodiment illustrated and described, the device includes an internal rechargeable battery that is charged by an induction charger. The primary induction circuit discussed below is housed between the bottom surface of the base and the top surface of the plate 316 (FIG. 26). The primary induction circuit is terminated at a fixed connector (not shown) that is accessible by way of a cut-out 322 in the bottom plate 316. An external connector 324 is configured to mate with the fixed connector. The external connector is connected to a cable that is connected to an external source of electric power.

As shown in FIG. 26, the base 308 is tipped on its side in order to illustrate a bottom plate 316, attached to the bottom of the base 308 by a pair of fasteners 318 and 320. As illustrated in FIG. 27B, the space between the bottom plate 316 and the bottom side of a top surface 317 (FIG. 25B) of the base 308 may be used to carry primary side of the charging circuit. In particular, several of the components including: a ballast block 421, steel block 428, a magnet switch 427, and a printed circuit board 429 are carried in the cradle portion 310 of the base 308. A socket 431 is accessible from the bottom of the base 308 for receiving the internal connector 322 (FIG. 26) for connection to an external power source (not shown). A magnet 404 carried by the device 300 is configured to be aligned with the steel block 428 when the device 300 is received in the cradle portion 310 of the base 306. This causes the magnetic switch 427 to trip to indicate that the device 300 is in position for charging. This causes a transmit coil 434 in the stand portion 312 (FIG. 25B) of the base 306 to be connected to the external source of power. The transmit coil 434 is positioned in the stand portion 312 of the cradle portion 310 so as to be aligned with a receive coil 435 formed in the handle portion 304 of the device 300. As such, when the device 300 is seated in the base 308 and the external connector 324 (FIG. 26) is connected to the socket 431 in the base 308 and to an external source of power, the power applied to the transmit coil 434 is coupled to the receive coil 435 by magnetic induction to charge an internal battery 403 carried by the device 300.

An exemplary blade assembly 330 is illustrated in FIG. 28. The blade assembly 330 may be injection molded around the blade and configured so that the body portion or blade holder 360 can slide between the rails 334 (FIG. 24B) of the dermaplaning device 300. The exemplary blade assembly 330 includes a body portion 360, a nose portion 362 and a may include a safety cage portion 364. Alternatively, the safety cage portion 364 may be formed as part of the blade. The nose portion 362 is formed to fit into a cut-out 366 in the base portion 306 (FIG. 24A) of the dermaplaning device 300. The safety cage portion 364 extends outwardly from the bottom of the body portion 360. The safety cage portion 364 is formed with a plurality of outwardly extending teeth, generally identified with the reference numeral 368. The teeth 368 extend substantially the entire length of the blade assembly 330. The teeth 368 are spaced apart. The blade 364 is disposed slightly below the tips of the teeth 368, for example, as illustrated and discussed in connection with FIG. 16*a*. In other words, the teeth extend farther out than the edge of the blade. The distance between the tips of the teeth 368 and the edge of the blade establishes the penetration of the blade. Typically, a penetration of several millimeters is suitable for non-professional use.

As will be discussed in more detail below, the body portion 360 of the blade assembly 330 is formed to cooperate with a blade assembly control mechanism, discussed below, to provide interlocks with respect to certain aspects of the control logic. In particular, in an exemplary embodiment, the control logic utilizes the configuration of the body portion 360 of the blade assembly 360 to perform one or more of the following functions: [0091] Determine whether the blade assembly 330 is fully inserted into the dermaplaning device 300. [0092]Determine whether the blade assembly 330 has been previously removed from the device 300.

Releasably "lock" the blade assembly 330 in a fully inserted position.

Figure 36:
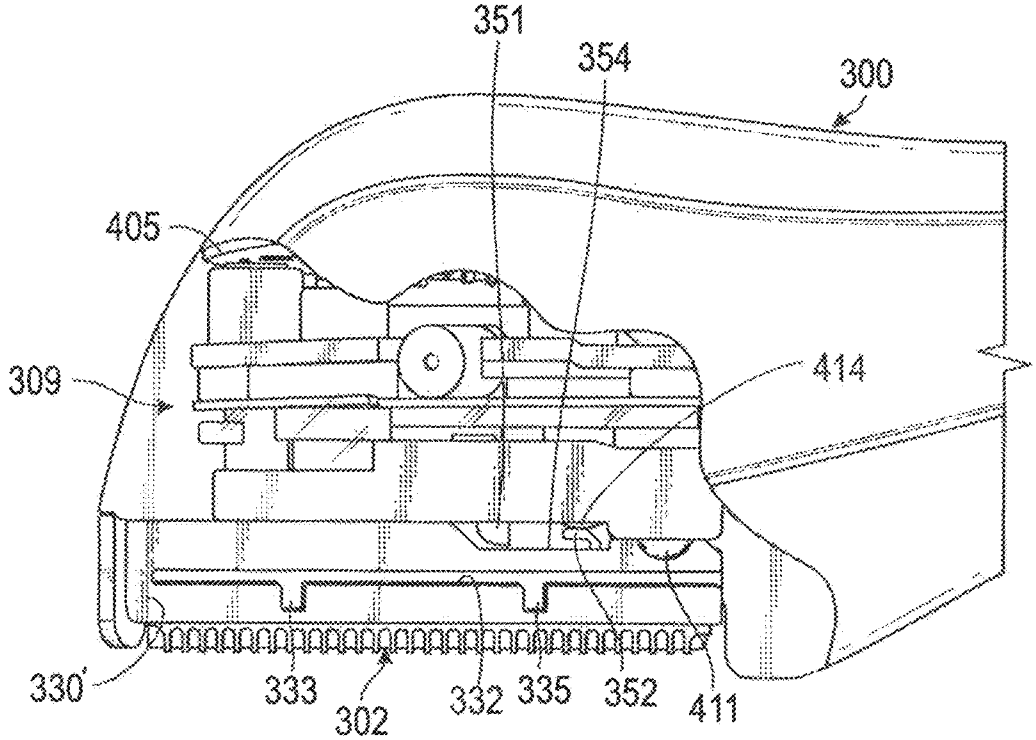
FIG. 36 is a partial side elevational view of one embodiment the dermaplaning device with a portion of the cover removed, illustrating a blade assembly control mechanism and shown with a blade assembly installed.
Figure 37:
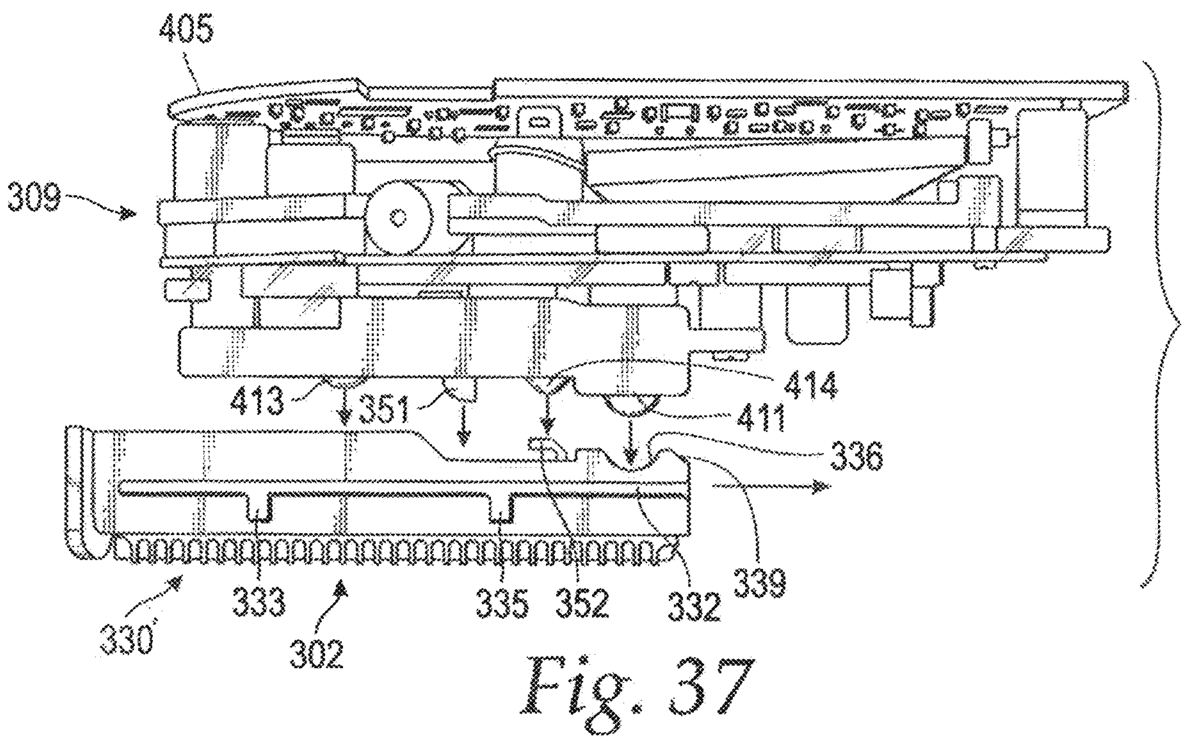
FIG. 37 is a side elevational view illustrating the relationship between a blade assembly control mechanism and a blade assembly.

Each of these functions are described in detail. Several of these functions are formed as interlocks. The interlocks are the result of interaction between the blade assembly 330 and the blade assembly control mechanism 309 (FIGS. 27A, 36 and 37). In particular, the body portion 360 of the of the blade assembly 330 may be configured to cooperate with one or more mechanisms in the blade assembly control mechanism 309 to provide one or more of the above-mentioned functions.

The blade assembly control mechanism 309 includes a body portion and one or more micro-switches 408, 409 responsive to one or more spring loaded bullet pins 413, 414 which form electrical interlocks. The bullet pins 413, 414 are biased downwardly. When the bullet pins 413, 414 are forced upwardly, the micro-switches 408, 409 are actuated.

The blade assembly control mechanism 309 may also include mechanical interlocks. For example, the blade assembly control mechanism 309 may include a spring loaded knife blade 422 that is biased downwardly. The spring loaded knife 422 is configured to break off the extending tab 352, as the blade assembly is being removed. On re-insertion of the blade assembly 330, the spring loaded bullet pin 414 is not moved upwardly and the micro-switch 409 is not actuated. The blade assembly control mechanism 309 may also include a one or more mechanical interlocks. For example, the blade assembly control mechanism 309 may also include spring loaded bullet pin 411 that is biased downwardly which cooperates with an arcuate notch 322 formed in the lower shelf surface 354 of the blade assembly 330 in order to create a locking mechanism that is released when the blade assembly 330 is removed from the device 300.

Various types of locking mechanisms are contemplated for locking the blade assembly 330 in place during use. An exemplary locking mechanism is illustrated in FIGS. 27A and 27B. FIG. 27A illustrates an enlarged partial sectional view of a head portion 307 of the dermaplaning device 300. FIG. 27B is similar to FIG. 27A but is more detailed and illustrates the head portion 307 of the dermaplaning device 300 seated in a base 308, as discussed above.

Referring first to FIG. 27A, an exemplary locking mechanism is illustrated as a spring loaded bullet pin 411 is carried by the blade assembly control mechanism 309. The bullet pin 411 is configured to cooperate with an arcuate notch 336, formed in the body portion 360 of the blade assembly 330. As the blade assembly 330 is slid into place, the spring loaded bullet pin 411 slides along the top surfaces of the body portion 360 of the blade assembly 330. As the blade assembly 330 approaches its fully inserted position, the spring force urges the bullet pin 411 downwardly until it is seated in the arcuate notch 336 formed at an end of the blade assembly 330, as shown in FIG. 27A, thus locking the blade assembly 330 in place.

In order to remove the blade assembly 330, a lateral force, opposite the insertion force, is applied to the blade assembly 330. The lateral force causes the bullet pin 411 to retract as its tip rides up the curved surface of the arcuate notch 336. Once the bullet pin 411 is free of the arcuate notch 336, the blade assembly 330 is essentially unlocked and the blade assembly 330 can be removed.

Positive indication may also be provided to the control logic, for the dermaplaning device 300 to indicate that the blade assembly 330 is fully inserted in the dermaplaning device 300. In particular, a pair of micro-switches 408 and 409 may be provided to provide a positive indication that the blade assembly 330 is fully inserted in the dermaplaning device 300. These micro-switches 408 and 409 are actuated by spring loaded bullet pins 411 and 414, respectively. In particular, the spring loaded bullet pin 411 is configured to actuate the micro-switch 408 while the spring loaded bullet pin 414 is configured to actuate the micro-switch 409. The bullet pins 411 and 414 ride along the top surfaces of blade assembly 330 as it is being inserted or removed from the dermaplaning device 300. In particular, as the blade assembly 330 is being inserted, the bullet pin 414 rides along an upper shelf surface 350 (FIG. 28) of the body portion 360 of the blade assembly 330 and initially activates the micro-switch 408. As the bullet pin 414 is moved past the upper shelf surface 350 and onto a lower shelf surface 354, the spring loaded bullet pin 414 is urged downwardly by the spring force, thus de-activating the micro-switch 408. As the blade assembly 330 is continuously inserted, the bullet pin 413 is biased upwardly by the tab 352 formed on an upper shelf surface 354 of the blade assembly, thereby actuating the micro-switch 414, which remains actuated while the blade assembly 330 is fully inserted into the dermaplaning device 300. At this point, both bullet pins 413 and 414 are biased upwardly, thereby actuating both micro-switches 408 and 409. As will be discussed below, the dermaplaning device 300 is inoperable until both micro-switches 408 and 409 are actuated.

The dermaplaning device 300 may also be configured so that a blade assembly 330 cannot be re-used once the blade assembly 330 has been removed from the device. Various mechanical interlock systems are contemplated for this function. An exemplary interlock system is illustrated in FIGS. 27A and 27B. For example, a spring loaded knife blade 422 extends downwardly from the blade assembly control mechanism 309 extends into the path of the blade assembly 330 as it is being inserted and removed from the dermaplaning device 300. A forward surface 353 of the knife blade 422 is formed with a cammed surface. As such, as the blade assembly 330 is being inserted, the extending tab 352 on the blade body 360 of the blade assembly 330 causes the knife blade 422 to push the knife blade 351 upwardly against the spring force. As the blade assembly 330 continues advancing toward a fully inserted position, the knife blade 422 returns to a normal position, as shown, under the influence of the spring.

When the blade assembly 330 is removed from the device, the tab 352 of the blade assembly 330 catches against a flat surface 355 of the knife blade 351. In order to remove the blade assembly 330, a sufficient lateral force must be exerted to break the tab 352 to allow the blade assembly 330 to be removed. After the tab 352 is broken off, the blade assembly 330 can continue to be removed. The surfaces 337 and 339 will slide under the knife blade 351 to allow the blade assembly 330 to be completely removed.

Once it is removed, the tab 352 will not be available on a re-insertion to activate bullet pin 414 and the micro-switch 409, thus preventing re-use of that blade assembly 330 and thus will not actuate the micro-switch 409 if the blade assembly 330 is re-inserted. As will be discussed in more detail, unless both micro-switches 408 and 409 are activated, the dermaplaning device 300 will not operate. Thus, the tab 352 prevents the blade assembly 330 from being re-used.

Alternatively, the upper shelf surface can be extended further along the length of the blade assembly 330 defining an extended upper shelf surface to actuate the bullet pin 411 and the micro-switch 409 as the blade assembly is being fully inserted and as it is being fully removed. This configuration results in a reusable blade assembly.

As described below, any blade assembly used with the device 300 must satisfy two interlocks or conditions. The first interlock relates to the micro-switch 408. This micro-switch 408 indicates that a blade assembly has been inserted into the device 300. As discussed below, the first interlock alone is insufficient to enable the device 300 to be started. The second interlock relates to the micro-switch 409. This second interlock indicates that the blade assembly is fully inserted. Both interlocks are required before the device 300 can be enabled. With reference to FIG. 27*a*, the second interlock is responsive to the spring loaded bullet pin 413. The spring loaded bullet pin 413 will actuate the micro-switch 409 only if the tab 352 is in place. Once the tab 352 is broken off, any attempts to reuse the blade assembly 330 will result in the bullet pin being unable to move upwardly to actuate the micro-switch 409.

Other variations of the blade assembly 330 illustrated in FIG. 28 are contemplated. Any blade assembly that includes a body portion 360 that is configured to be inserted and removed from the dermaplaning device 300 and satisfy both interlocks with the blade assembly control mechanism 309, i.e. actuate micro-switches 408 and 409, is considered to be within the broad scope of the invention.

An exemplary alternative embodiment of the blade assembly 330 is illustrated in FIGS. 41 and 42 and identified with the reference numeral 330'. The blade assembly 330' lends itself to be re-used while still satisfying the various interlocks of the blade assembly control mechanism 309 that allow the device 300 to work.

Figure 32:
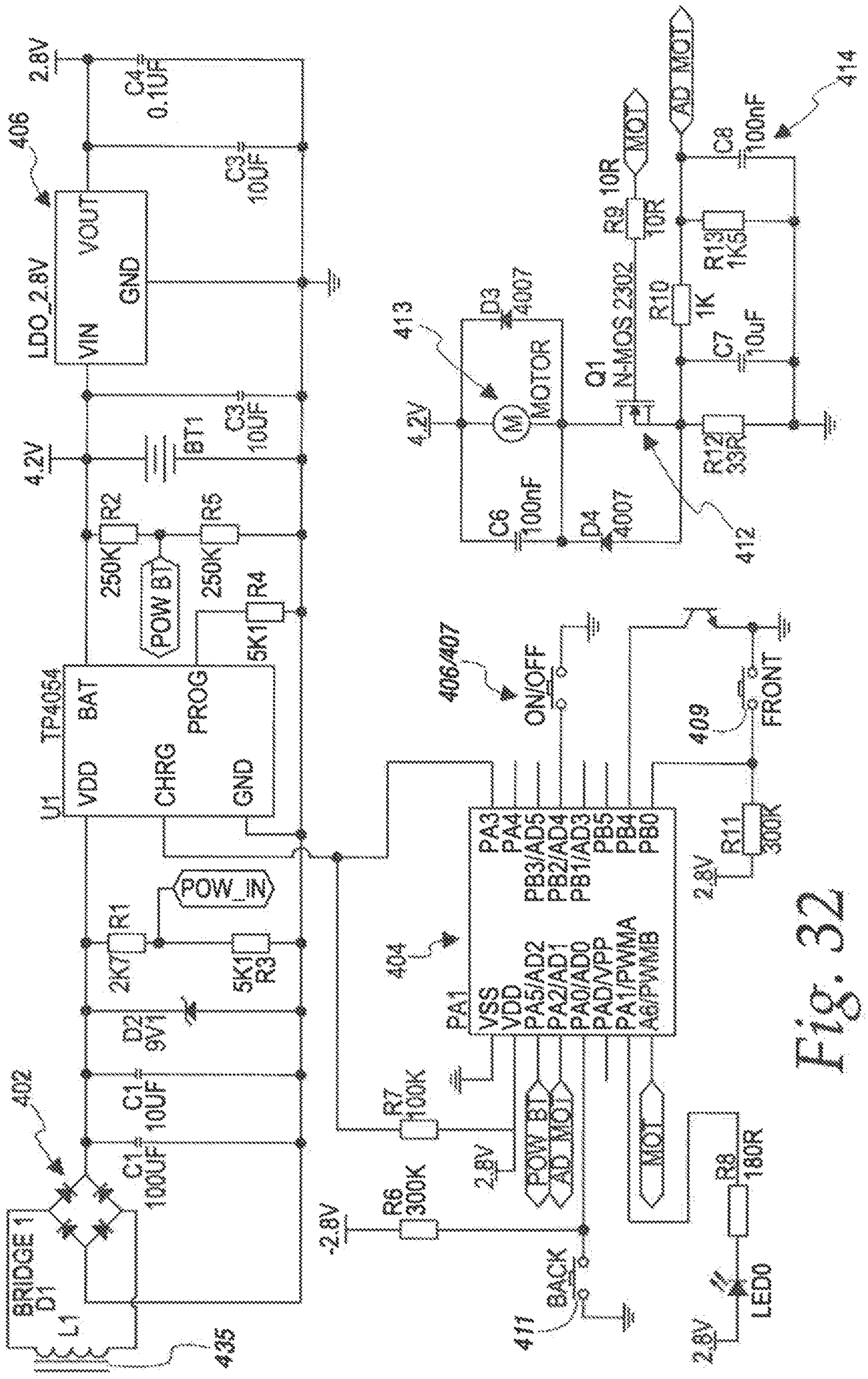
FIG. 32 is an exemplary electrical schematic drawing of the dermaplaning device illustrated in FIG. 21.

FIG. 41 illustrates an exemplary embodiment of the alternative blade assembly 330' fully inserted into the device 300 while FIG. 32 illustrates the alternative blade assembly 330' in the process of being removed. Referring first to FIG. 41, the tab 352 in the blade assembly 330, illustrated in FIG. 28, is replaced with a ramp 352'. The configuration of the alternative blade assembly 330' satisfies bath interlocks discussed above. As the blade assembly 330' is being inserted, the spring loaded knife blade 351 and the bullet pin 414 slide up the ramp 352'. As the blade assembly 330' reaches the fully inserted position as shown in FIG. 41, the bullet pin 414 reaches the apex of the ramp 352'. This causes the bullet pin 414 to move upwardly and actuate the micro-switch 409 to indicate that the blade assembly 330' is fully inserted, thus satisfying the second interlock, discussed above. As the blade assembly 330' is removed, as indicated in FIG. 42, the spring loaded knife blade 351 rides up the ramp 352' allowing the blade assembly 330' to be removed. The blade assembly 330' can be re-inserted, as discussed above.

The alternative blade assembly 330' also satisfies the first interlock. With reference to FIGS. 41 and 42, the alternative blade assembly 330' also includes a body portion 360' having a top shelf 350', similar to the blade assembly 330. As such, as the alternative blade assembly 330' is inserted into the device 300, the bullet pin 411 contacts the top shelf 350' of the alternative body portion 360', which, in turn, actuates the micro-switch 408 thus satisfying the first interlock.

In order to be useable with the device 300, any alternative blade assembly must be able to satisfy the two interlocks discussed above. In other words, any alternative blade assembly must be able to actuate the limit switches 408 and 409 when inserted. As discussed above, embodiments are contemplated which allow the blade assembly to be re-used after it has been removed from the device. Other embodiments are contemplated that do not include the locking feature. In these embodiments, the alternative body portion 360, is formed without an arcuate notch 336, as discussed above, in these embodiments, the spring loaded bullet pin 413 would simply rest on a surface other than an arcuate surface that provides a locking feature.

FIGS. 36 and 37 illustrate a simplified drawing of the blade assembly control mechanism 309. FIG. 36 illustrates the blade assembly 330 fully inserted. FIG. 37 illustrates the blade assembly 330 (FIG. 28) removed from the blade assembly control mechanism 309. The blade assembly control mechanism 309 is configured to carry one or more of the spring loaded bullet pins 411, 413 and 414 and the spring loaded knife blade 351. The blade assembly control mechanism 309 may also be configured to carry the micro-switches 408 and 409. As mentioned above, the micro-switch 408 is responsive to the bullet pin 413 while the micro-switch 409 is responsive to the bullet pin 414. The micro-switches 408 and 409 as well as the battery charging circuit and control circuit illustrated in FIG. 32 are connected together by way of a printed circuit board (PCB) 405 (FIGS. 36 and 37) carried by blade assembly control mechanism 309.

Figure 33:
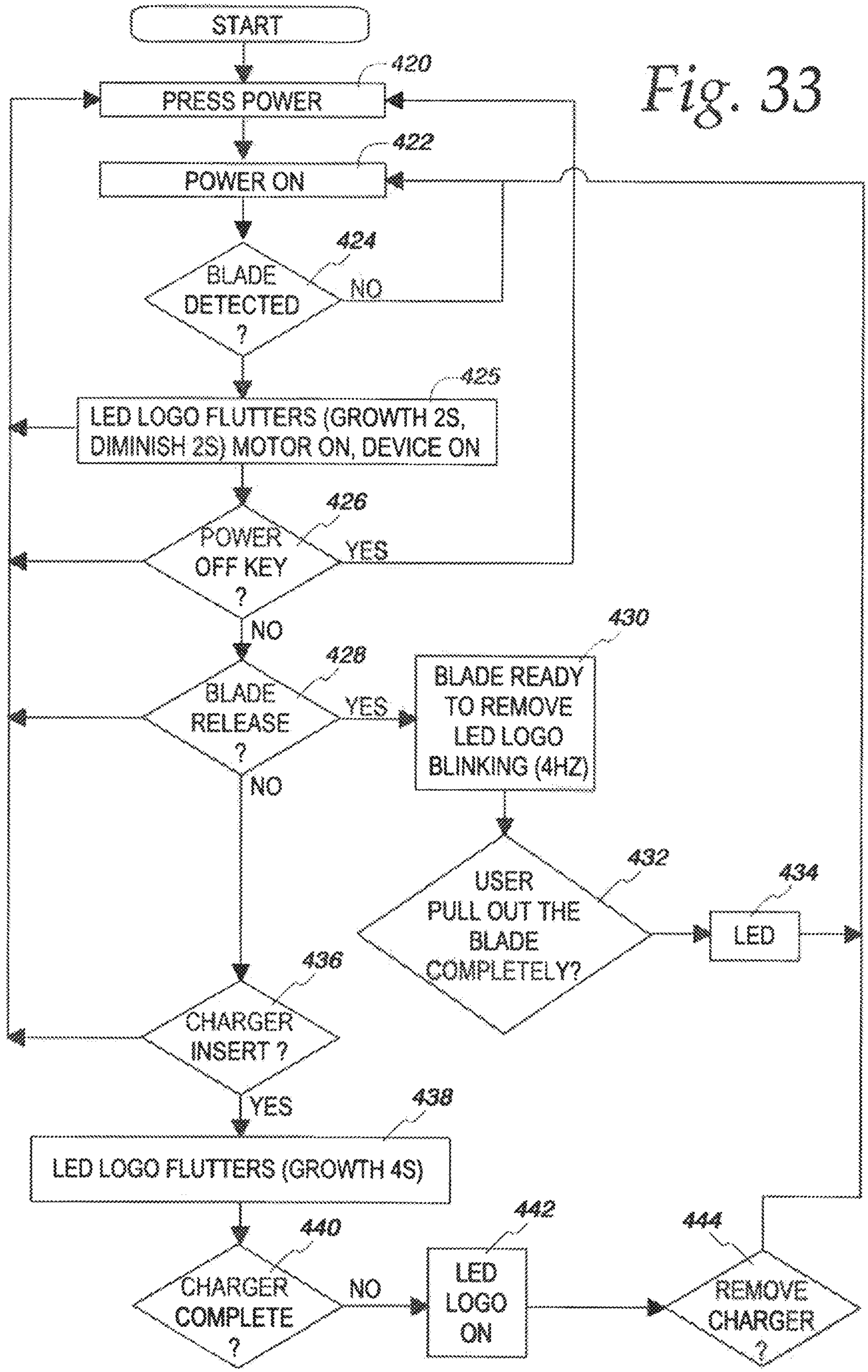
FIG. 33 is an exemplary software flow diagram of the for exemplary dermaplaning device illustrated in FIG. 21.
Figure 34:
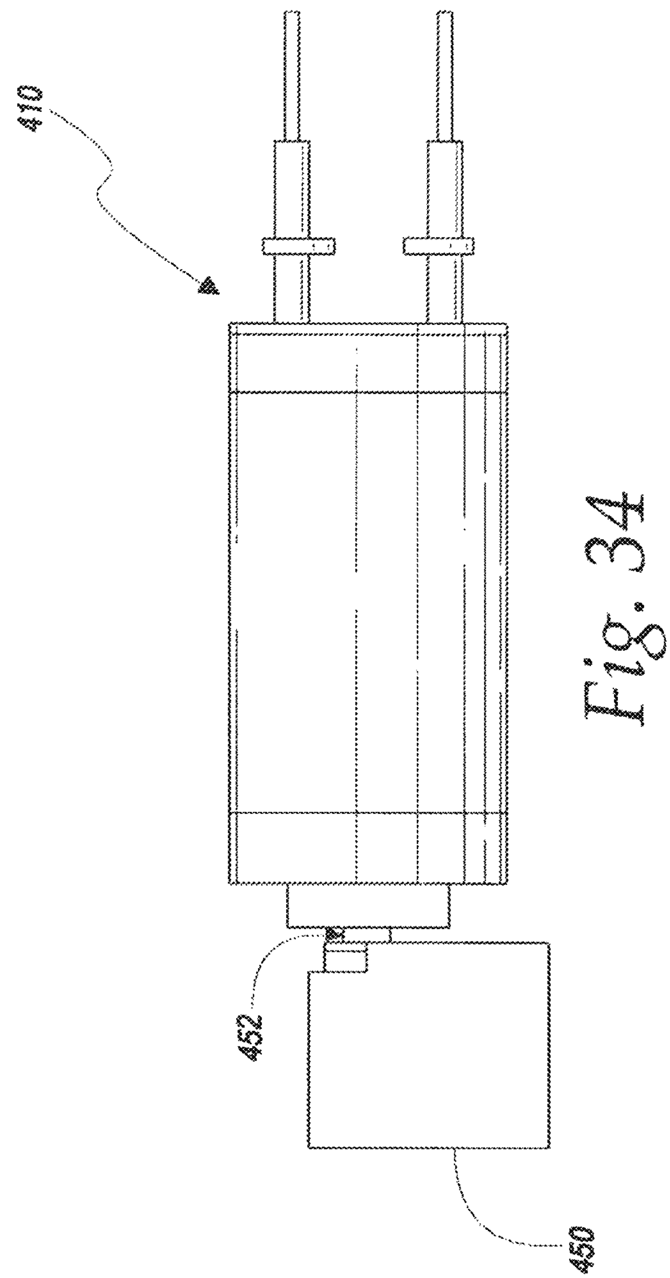
FIG. 34 is a side elevational view of an exemplary vibration generator for use with the present invention.

An exemplary electrical schematic diagram and an exemplary software logic flow diagram are illustrated in FIGS. 32A and 33, respectively. Turning first to FIG. 32A, an exemplary embodiment of a battery charging circuit is illustrated. In particular, the battery charging circuit is coupled to an external source of electric power by magnetic induction. In particular, a primary winding (not shown) is disposed in the base 308 (FIG. 26). The device 300 is charged by magnetic induction charging and includes a receive coil 435 (FIG. 27B) in the device 300 that cooperates with a transmit coil 434 in the cradle portion of the base 308. As mentioned above, the transmit coil 434 (FIG. 27B) as well as the balance of the primary circuit are carried by the cradle portion 310 of the base 308. When the device 300 is fully seated in the cradle portion 310 of the base 308, a magnetic switch 427, located in the base 308 will detect the magnet 404 located in the belly of the device 300 and will connect the primary winding 434 to the socket 431. If the connector 324 is connected to a socket 431 and to an external source of power, a voltage will be induced in the secondary winding 400 (FIG. 32), which in turn, is connected to a battery charger circuit for charging the internal battery 403. The components of the primary side of the magnetic induction circuit are connected together by way of a PCB 429, located in the cradle portion 308 of the base 306.

An exemplary configuration for the primary winding diameter 434 and the secondary winding 435 diameter (FIG. 27B) is 16 mm by 3 mm with a maximum coupling distance of 5 mm. The secondary winding 435 is connected to a bridge rectifier 402 which includes four diodes. The output of the bridge rectifier 402 is an unregulated DC voltage that is connected to a battery charger U1, for example, a lithium ion constant current/constant voltage battery charger, Model No. TP054. A pair capacitors C1 and C2 are connected across the output of the bridge rectifier 402 to stabilize the voltage to the battery charger UL. In addition, a Zener diode D2 is also connected as a shunt regulator across the output of the bridge rectifier 402 to protect the battery charger U1 from voltages above the Zener voltage. A pair of series connected resistors R1 and R3 are also connected across the rectified 402 output. These resistors form a voltage divider and are used to generate a signal <POW IN> representative of the voltage applied to the battery charger U1. This signal <POW IN> is used to indicate to a microprocessor 404, for example, a Tenx Model No. TM57/PA10A-SOP16, that the charging circuit is connected to an external source of power.

A positive rail of the bridge rectifier 402 is connected to a voltage terminal VDD on the battery charger U1. A negative rail of the bridge rectifier 402 is connected to a ground terminal GND on the battery charger U1. A charge status terminal CHRG on the battery charger U1 is used to indicate the state of charging. This terminal CHRG is applied to the microprocessor 404 and is pulled low during battery charging and is thus used to indicate to the microprocessor 404 the presence of a charging cycle. A terminal BAT, connected to a positive rail of the battery 403 for charging. A pair of voltage divider resistors R2 and R5 is connected across the battery 403 to develop a signal <POW BT>. This signal <POW BT> is fed to the microprocessor 404.

The battery 403 is connected across the positive and negative rails of the charging circuit. Anytime, the battery 403 falls below 2.9 volts DC, the battery charger U1 causes a trickle charge to be applied to the battery 403 until the battery 4031 reaches 2.9 volts DC. The battery charger U1 then enters a constant current mode. The charging current is programmable and is programmed by the resistor R4 attached to the PROG terminal of the battery charger U1.

A voltage stabilizing capacitor C3 is connected across the input of a voltage regulator 406. The positive rail is also connected to an input terminal Vin on a voltage regulator 406. The voltage regulator 406 regulates the output voltage of the battery to a nominal 2.8 volts DC. The 2.8 volt DC output is available at an output terminal Vout of the regulator 406. A ground terminal GND on the voltage regulator 406 is connected to system ground. A pair of capacitors C3 and C4 is connected between the output terminal Vout on the voltage regulator 406 and system ground. These capacitors C3 and C4 are connected in parallel and are used to stabilize the output voltage at the output terminal Vout of the regulator 406.

The microprocessor 404 controls the dermaplaning device 300. The microprocessor 404 receives inputs from the micro-switches 408 and 409 (FIG. 27A), the state of charging by the battery charger U1, the battery voltage, whether the on-off switch is actuated and whether the dermaplaning device 300 is being charged by the charging cradle portion 308. In particular, a CHRG signal from the battery charger U1 is applied to a port PA3 of the microprocessor 404. The CHRG signal is low when the battery charger U1 is charging the battery 403. The signal CHRG is also applied to a VDD pin of the microprocessor 404 by way of a current limiting resistor R7. During conditions when the battery 403 is not charging the pin VDD is pulled up by way of 2.8 volts DC. During charging, the pin VDD is pulled low indicating that the battery 403 is not fully charged. The signal <POW IN> is applied to a transistor switch Q2. When input power is available, as indicated by the <POW IN> signal, the voltage regulator 406 and a current limiting resistor R11. When the micro-switch 409 is engaged as the blade assembly 330 is inserted into the dermaplaning device 300, the switch 408 closes pulling the port PB0 low. The micro-switch 408 is connected to a port PA0. In particular, port PA0 is normally pulled high by way of a 2.8 volt DC signal from the voltage regulator 406 and a current limiting resistor R6. When the micro-switch 409 is engaged as the blade assembly 330 is inserted into the dermaplaning device 300, the switch 406/407 closes pulling the port PA0 low. An on-off switch 406/407 is connected to port PB2 of the microprocessor 404. When the switch 406/407 is depressed, the port PB2 is pulled low, causing the motor 413 to be turned on, as discussed below.

As will be discussed below in connection with the control logic, the microprocessor 404 outputs a signal <MOT> to control the motor 413 that forms part of a vibration generator. The microprocessor 404 also controls LED0. The LED0 is connected between the output voltage of the regulator and a port PA1 by way of a current limiting resistor R8. The microprocessor 404 also develops a feedback signal <AD MOT> that is used to stabilize the vibration and to make it independent of the battery level.

An exemplary motor control circuit is illustrated. As shown, the motor 413 is powered from 4.2 volts DC, available at the positive terminal of the battery 403. The motor 413 is connected between the 4.2 volts DC and ground by way of a switching circuit and a feedback circuit. The motor 413 is connected between 4.2 volts DC, available at the battery 403 and ground by way of a switch circuit 412 and a resistor R12. The switch circuit 412 includes a switching transistor Q1 that is driven by the <MOT> signal by way of a current limiting resistor R9. When the signal <MOT> is asserted by the microprocessor 404, the transistor switch Q1 will cause the motor 413 to be connected to ground by way of the resistor R12, thus turning the motor on. A capacitor C6 stabilizes the voltage to the motor. When the motor 413 is turned off, a free-wheeling diode D3 provides a current path. The diode D4 blocks the motor current from bypassing the switching circuit 412.

A feedback circuit 414 stabilizes the operation of the motor 413 and essentially isolates it from the level of the battery 403. Nominally, the battery 403 is at 4.2 volts DC. Once the motor 413 is turned on, a feedback signal <AD MOT> goes high and applies about 2.8 volts DC across the resistor R13. A capacitor C8 stabilizes this voltage. The resistors R10 and R13 form a voltage divider to provide a portion of the 2.8 volts from the <AD MOT> signal across the resistor R12. The voltage across R10 is stable and is applied to the resistor R12. The capacitor C7 stabilizes the voltage applied to the resistor R12. The constant voltage across R12 will cause a constant current to flow through the motor 413 irrespective of the level of the battery 403. The constant current will cause the motor to operate at a constant speed since the speed of a DC motor is proportional to current.

Figure 3:
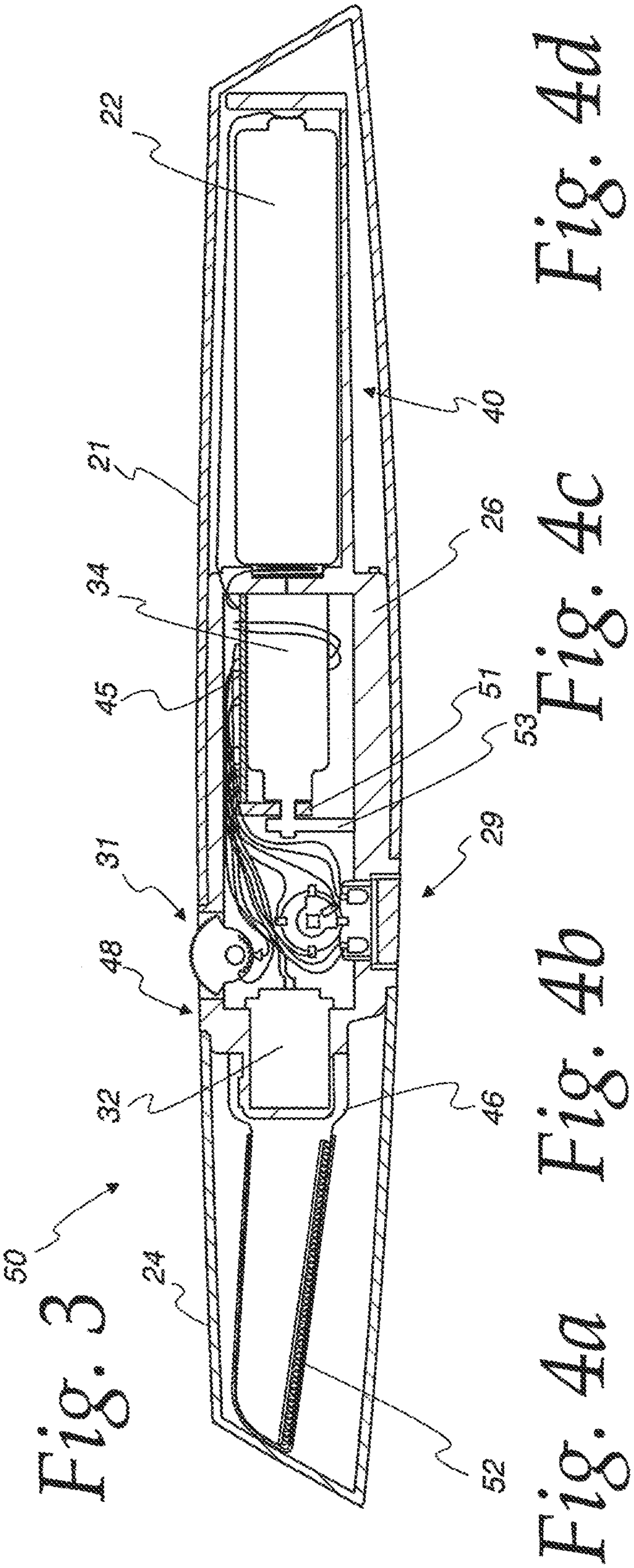
FIG. 3 is side elevational view in section of the dermaplaning device illustrated in FIG. 1.

The software flow diagram that is executed by the microprocessor 404 (FIG. 3 is illustrated in FIG. 33. Initially, when the on/off switch 406/407 (FIG. 27B) is depressed in step 420, battery power is connected to the dermaplaning device 300, as indicated in step 424. Next in step 424, the system checks whether a blade assembly 330 is detected. More particularly, the system checks whether the micro-switches 408 and 409 (FIG. 27A) have been actuated-indicating that a blade assembly 330 has been full inserted into the device 300. If a blade assembly has not been detected, the system loops back to step 422 and keeps checking for the insertion of the blade assembly 330. Once a blade assembly 330 is inserted into the device 300, the motor 413 is started in step 424. In particular, the microprocessor 404 generates a <MOT> which is applied to gate of the transistor Q1 to turn the transistor Q1 on. This completes the circuit from the 4.2 volt supply voltage through the series motor to the ground by way of the resistor RU. The microprocessor 404 also generates the <AD MOT> signal to stabilize the speed of the motor 404 and isolate the speed of the motor 404 from the voltage of the battery 403. In addition, the microprocessor 404 illuminates the LED0 and causes it to blink with two long and two short pulses.

The system checks in step 426 whether the on/off switch 406/407 (FIG. 27A) has been switched off. If so, the system loops back to step 420 and waits for the switch 406/407 to be turned back on. If the switch 406/407 has not been turned off, the system checks in step 428 whether the blade assembly 330 has been at least partially released. In particular, as the blade assembly 330 is partially removed to the point the micro-switch 409 (FIG. 27A) is de-actuated, the microprocessor 404 causes the LED0 to blink at 4 KHz in step 430. As the blade assembly 330 is removed to the point the second micro-switch 408 is de-actuated, as indicated in step 432, the LED0 is turned steady on in step 434. The system then loops back to step 422 and waits for the blade assembly 330 to be detected.

After the system checks whether the on/off switch 406/407 has been depressed in step 426 and after the system the system checks whether the blade assembly 330 is fully inserted into the device 300 in step 428, the system checks in step 436 whether an external source of power has been connected to the primary winding 434 of the charger circuit, the voltage VDD is detected by the microprocessor 404 by way of a power in signal <POW IN>. The power in signal <POW IN> is a signal at the junction of the series connected resistors R1 and R3. The serially connected resistors R1 and R3 are in parallel with the output if the bridge rectifier 402. Thus, anytime an external source of power is connected to the primary winding 434 (FIG. 27A), the power is induced in the secondary winding 435, which causes an AC voltage across the resistors R1 and R3. This voltage, in turn, causes the signal <POW IN> to have a positive voltage indicating that the external power has been applied to the primary winding 434 and that the primary winding 434 is in the cradle 308 to cause the voltage on the primary winding 434 to be coupled to the secondary winding 400, as indicated in step 436. Once a voltage on the secondary winding 435 has been detected, the microprocessor 404 causes the LED0 to blink with four (4) long pulses in step in step 438.

The system also determines when the battery charge is complete. This is done by monitoring the CHRG pin on the battery charger as indicated in step 440. Once the charge is complete, the microprocessor 404 turns the LED0 steady on in step 442 to indicate that the external source of power may be disconnected in step 444. Once the external source of power is removed, the signal <POW IN> goes low causing the system loops back to step 422.

FIG. 34 provides exemplary details for the vibration generator. In particular, the vibration generator 450 includes a motor 452 having a shaft 452 and a counterweight 454. The counterweight 454 is eccentrically configured and is attached to the motor shaft 452 so as to rotate with the motor shaft 452 without slippage. As the motor shaft 452 rotates, the counterweight 454 rotates. Because the counterweight 454 is eccentrically, i.e. not symmetrically, disposed relative to the motor shaft 452, rotation of the counterweight 454 causes vibrations to be transferred to the blade assembly 330, thus causing the blade assembly 330 to vibrate.

The counterweight 450 may be 3 mm in length and have a radius of 1.9 mm. The speed of the motor 440 is 10,000 RPM. As such, when the motor is energized with 1.5 volts DC and an operating current of 50 mA, the vibration generator 450 generates sub-sonic frequencies.

With reference to FIG. 27B, the dermaplaning device 300 includes a top housing portion 401 and a base housing portion 430. These housing portions 401 and 430 may be fastened together by various conventional means. For example, screws may be used and covered with screw covers, such as the screw cover 432. The sides of the housing are shown in FIGS. 24A and 24B The top of the housing is shown in FIG. 23.

An exemplary blade retainer 370 is illustrated in FIGS. 29-31. The blade retainer 370 is used to carry extra blade assemblies 330. As shown in FIG. 29, the exemplary blade retainer 370, as shown, includes an exemplary six (6) slots 372 for carrying six (6) blade assemblies 330. The blade assemblies 330 and 330" are oriented in the blade retainer 370 to enable the blade assemblies 330" to be loaded directly into the dermaplaning device 300 without requiring the user to touch the blade assembly 330". As shown in FIGS. 31-33, the blade retainer 370 is formed in an exemplary oval shape with the slots 372 formed perpendicular to the major axis of the oval.

Figure 38:
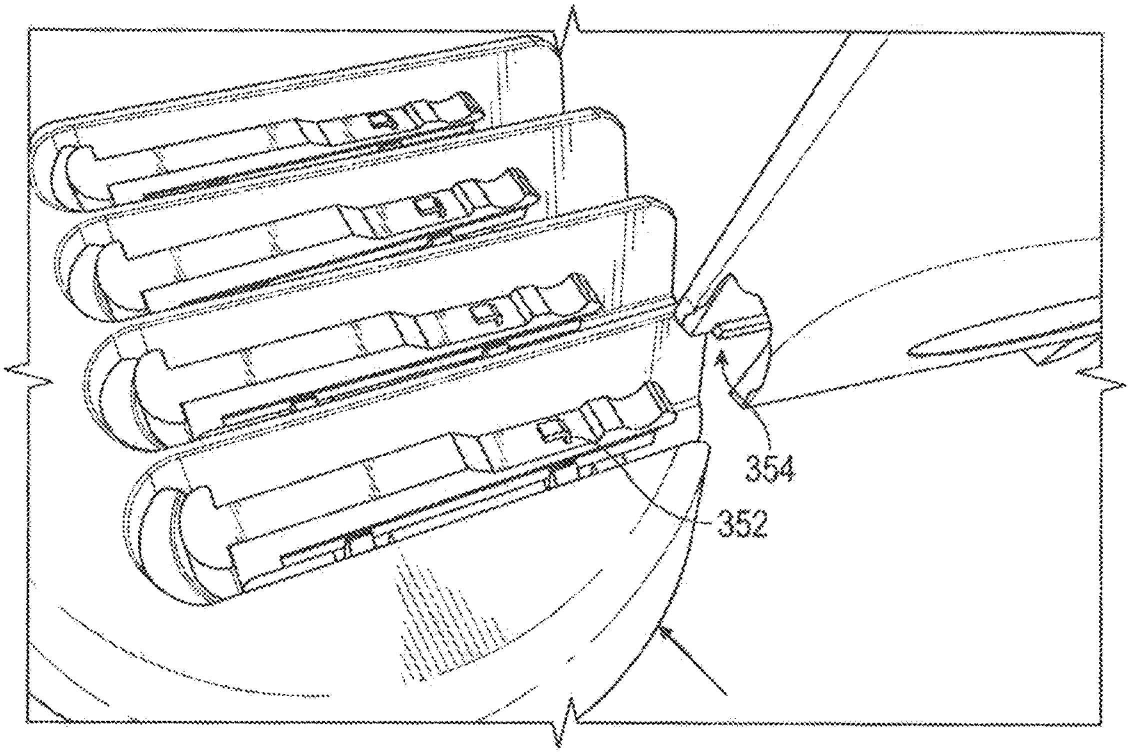
FIG. 38 is a partial isometric view of an alternate embodiment of the blade retainer illustrated in FIG. 29, shown loaded with blade assemblies, also shown with a partial isometric view of the dermaplaning device illustrated in FIG. 24B about to load a blade assembly.
Figure 39:
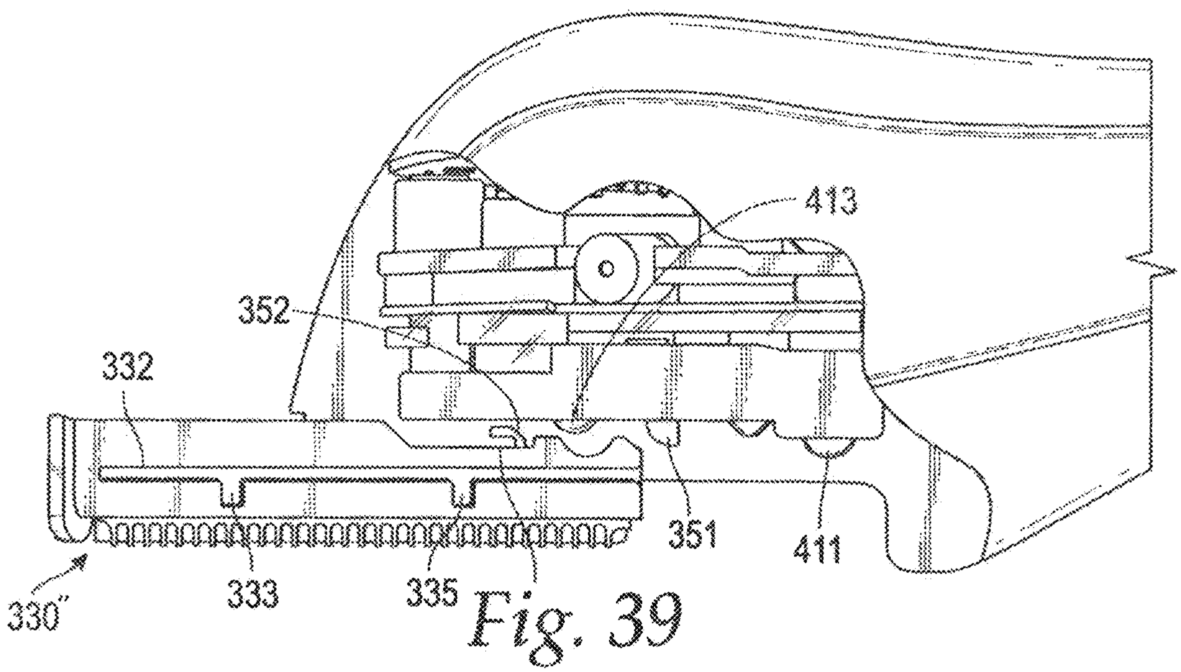
FIG. 39 is a partial side elevational view with a portion of the housing removed, also shown with a blade assembly partially loaded into the dermaplaning device.
Figure 40:
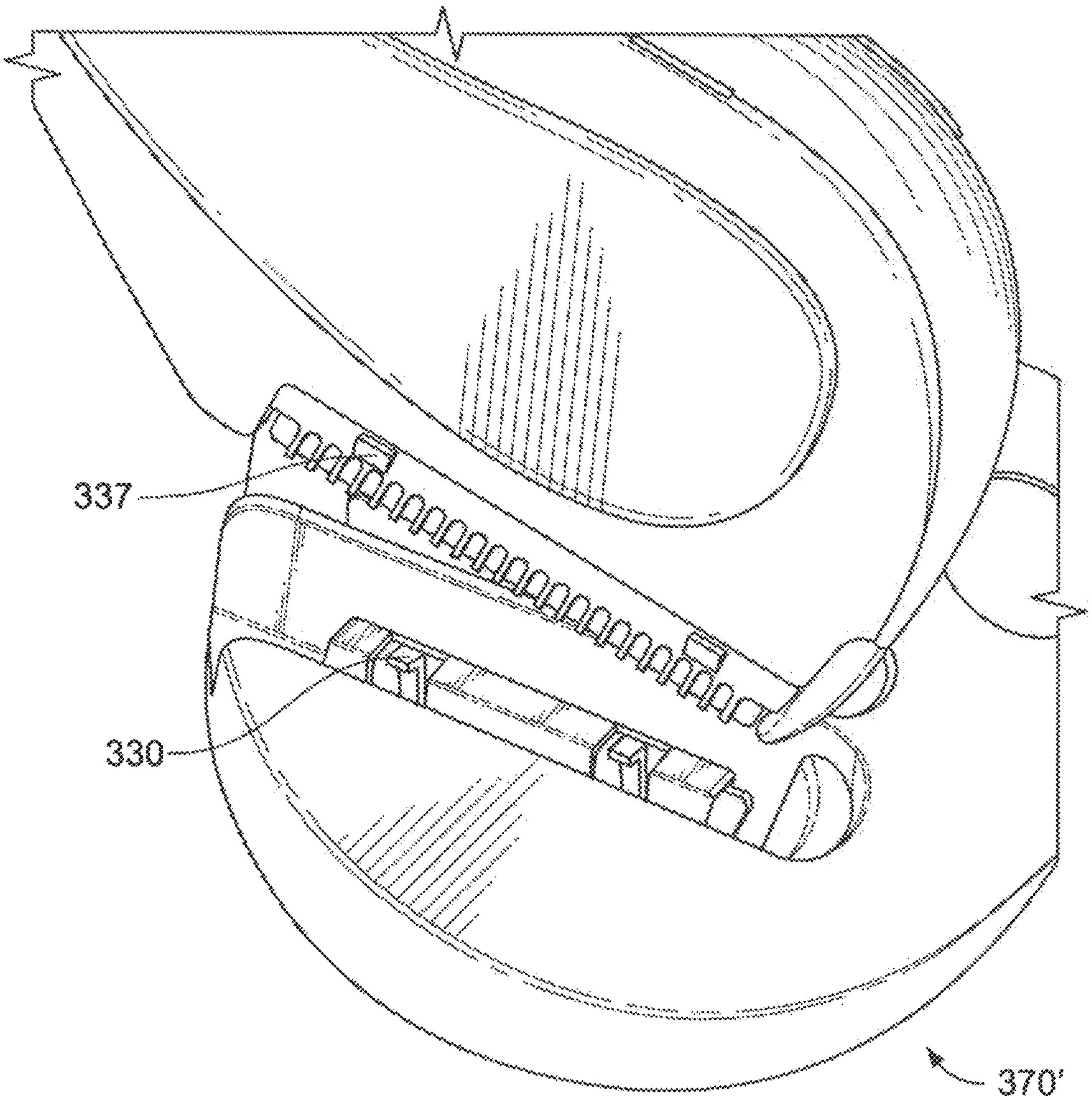
FIG. 40 is a partial isometric view of a dermaplaning device after a blade assembly has been fully loaded, shown with the dermaplaning device removed from the blade retainer.

Referring to FIGS. 38-40, an alternate embodiment of the blade retainer 370 illustrated in FIGS. 29-31 is includes a plurality of slots 372 for carrying alternative blade assemblies 330", as best illustrated in FIG. 39. As shown best in FIG. 39, each blade assembly 330" includes one or more notches 333, 335 (FIG. 39) adjacent the slots 332 (FIG. 28) on each side of the blade assembly 330. These notches 333, 335 (FIG. 39) cooperate with one or more "L" shaped arms 337 (FIG. 40) adjacent the slots 372 (FIG. 29) in the blade retainer 370' which have an extending horizontal leg portion 339 (FIG. 38) that is configured to be received in the notches 333 (FIG. 39) on each side of the slots 372 in the blade retainer 370 which hold both sides of the of blade assembly 330" (FIG. 28).

The "L" shaped arms 339 (FIGS. 38 and 40) are beneath the slots 332 on the sides of the blade assembly 330" (FIG. 28). This configuration enables the rails 334 (FIG. 38) on the device 300 to be received in the slots 332 on the blade assembly 330", as generally shown in FIGS. 38 and 39.

FIG. 38 illustrates a blade assembly 330" just before being loaded into a device 300. In order to load a blade assembly 330" into the device 300, the rails 334 on the device 300 are aligned with the slots 370 on the blade assembly 330". The device 300 is then inserted toward the blade retainer 370' to enable the rails 334 to be received in the slots 370 on the blade retainer 370'. Once, the rails 334 on the device 300 are received in the slots 370, the device 330 is moved toward the nose 362 of the blade assembly 330", as shown in FIG. 39. When the blade assembly 330' is fully loaded, the device 300 is removed from the blade retainer 370'. The "L" shaped legs 337 are flexible and allow the blade assembly 330" to be removed from the blade retainer 370' with little upward force.

The symmetry of the device 300 makes it suitable for easily treating both the left and right sides of a person's face. The handle portion 304 (FIG. 21) is angled to be 40.degree. to 60.degree. with respect to the horizontal, preferably 50.degree. In addition, the device 300 is contoured to treat both sides of a person's face in a downward motion. To treat the right side of a person's face, the device 300 may be held with a person's right hand. Similarly, to treat the left side of a person's face, the device may be held with the persons left hand.

Embodiments One Through Three

Outer Housing

As mentioned above, FIG. 1 illustrates an exemplary outer housing, generally identified with the reference numeral 20 that can be used with the various embodiments that include piezo-electric crystal and circuit and/or a motor and an optional rheostat for controlling the speed of the motor, for example, illustrated in FIGS. 2-6 and FIGS. 12-15. The outer housing 20 may be formed as a cylindrical hollow member closed on each end and formed in two parts by way of injection molded plastic, for example, or other material. Specifically, the outer housing 20 includes an end cap 21 which forms a handle portion and a top cap 24 which forms a cover portion. The cover portion 24 may be configured to attach to a main housing 26, discussed below, at a parting line 27. The handle portion 21 attaches to the main housing 26 at a parting line 30. In this exemplary embodiment, an on-off switch and optional integrated LED (light emitting diode), generally identified with the reference numeral 29, for controlling power to the device is carried by the main housing 26 and may be exposed between the handle portion 21 and the cover portion 24. As discussed in more detail below, an optional thumb wheel control switch 31, carried by the main housing 26, may be used to control the speed of the motor 34.

Figure 7:
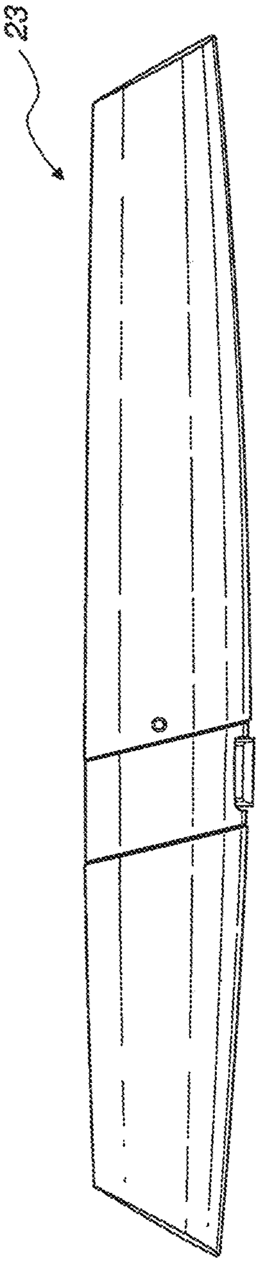
FIG. 7 is similar to FIG. 1 but without the thumb-wheel.
Figure 8:
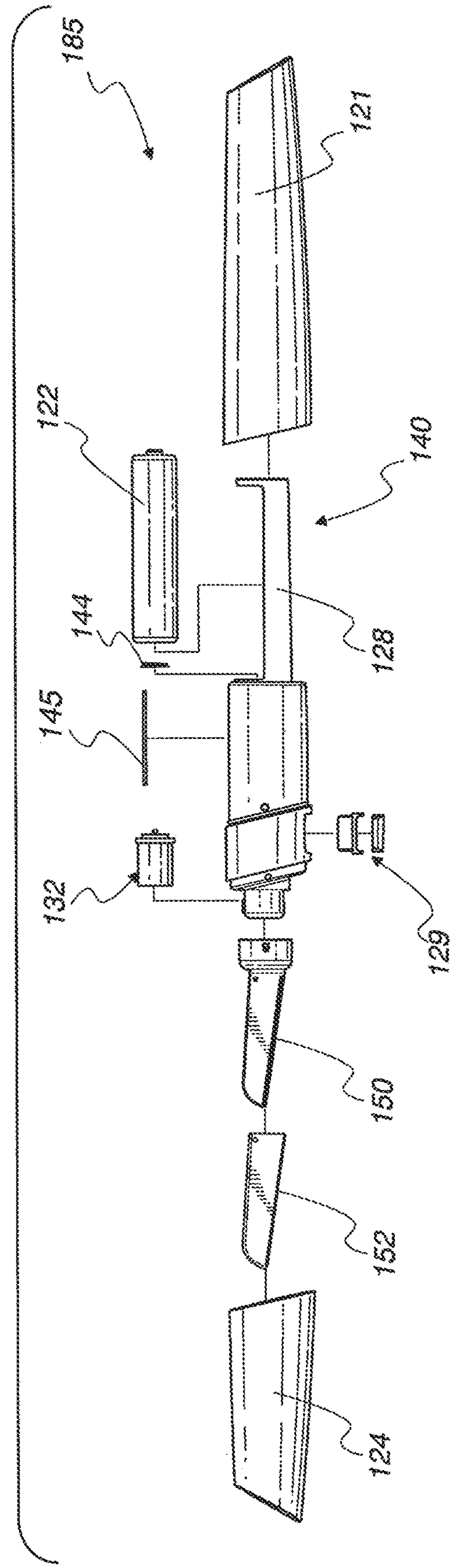
FIG. 8 is an exploded view of an alternate embodiment of a dermaplaning device that only includes a piezoelectric crystal.
Figure 9:
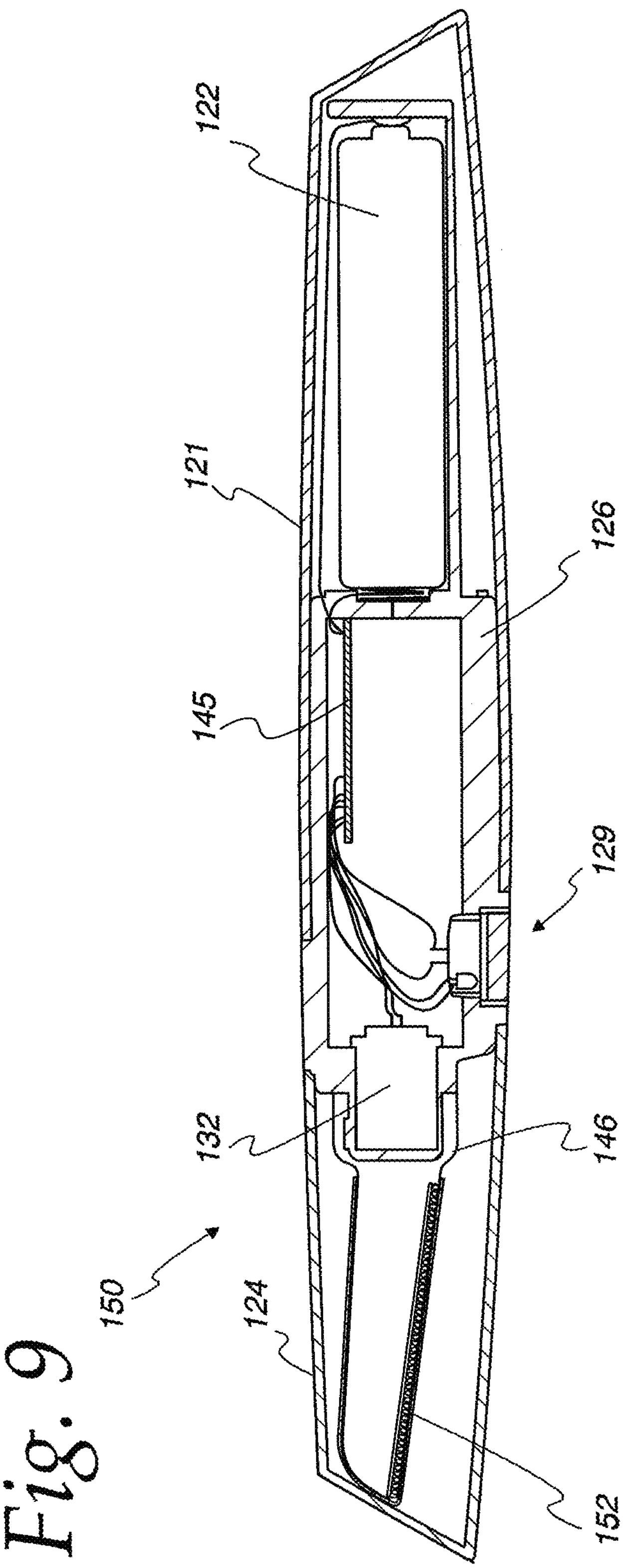
FIG. 9 is side elevational view in section of the dermaplaning device illustrated in FIG. 8

FIG. 7 illustrates an alternative outer housing, generally identified with the reference numeral 23. The outer housing 23 is used in embodiments that do not include a rheostat and optional thumbwheel.

As used herein, the term housing refers to the outer housing 20 (FIG. 1) and 23 (FIG. 7) individually as well as the combination of the outer housing 21, 23 in combination with the main housing 28 (FIG. 2), individually and collectively.

Various embodiments of the blade assembly are contemplated. For example, FIGS. 13*a*-13*f* illustrate an embodiment with a 2 piece blade assembly which includes a scalpel and a removable blade. In this embodiment, the scalpel may be fixedly mounted to the main housing or alternatively may be coupled to the main housing with a bayonet mount or other conventional coupling means.

First Embodiment

Referring first to FIGS. 2-6, a first embodiment of the invention is illustrated and described and identified with the reference numeral 85. The first embodiment of the invention includes a main housing 28, a piezo-electric crystal 32, a DC motor 34, an eccentric rotary load 36, coupled to a shaft 38 and a power supply, such as a battery 22. It is further contemplated that the power supply for the device can be an alternating current power supply. Such alternating current power supplies are well known in the art.

The main housing 28 may be made from an electrically conductive material forming a battery holder portion, generally identified with the reference numeral 40 defining a positive battery contact 42 and a negative battery contact 44. As will be discussed in more detail, below, a portion of the wiring between the various devices can be accomplished by way of a printed circuit board 45 which may be formed from a flexible printed circuit board Alternatively, the printed circuit board 45 may be omitted and the connections between the various devices can be made with electrical wiring.

Figure 16A:
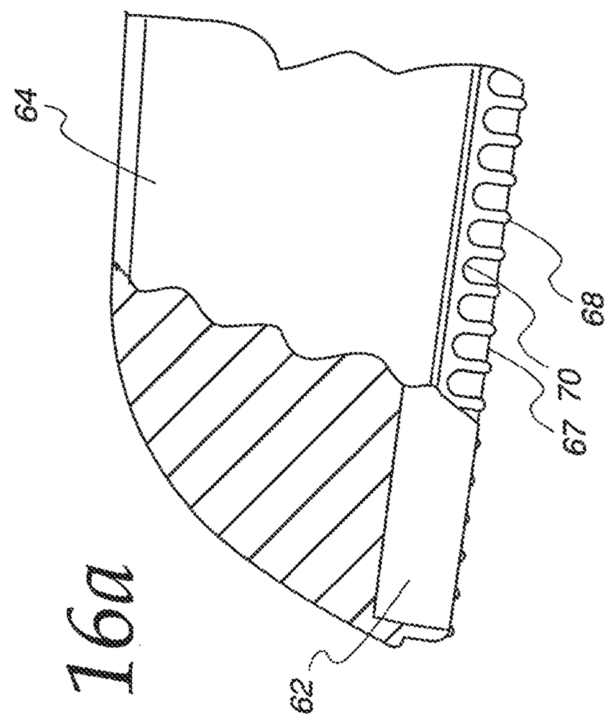
FIG. 16*a* is an enlarged partial view of the blade illustrating the safety cage and an exemplary blade assembly.
Figure 17:
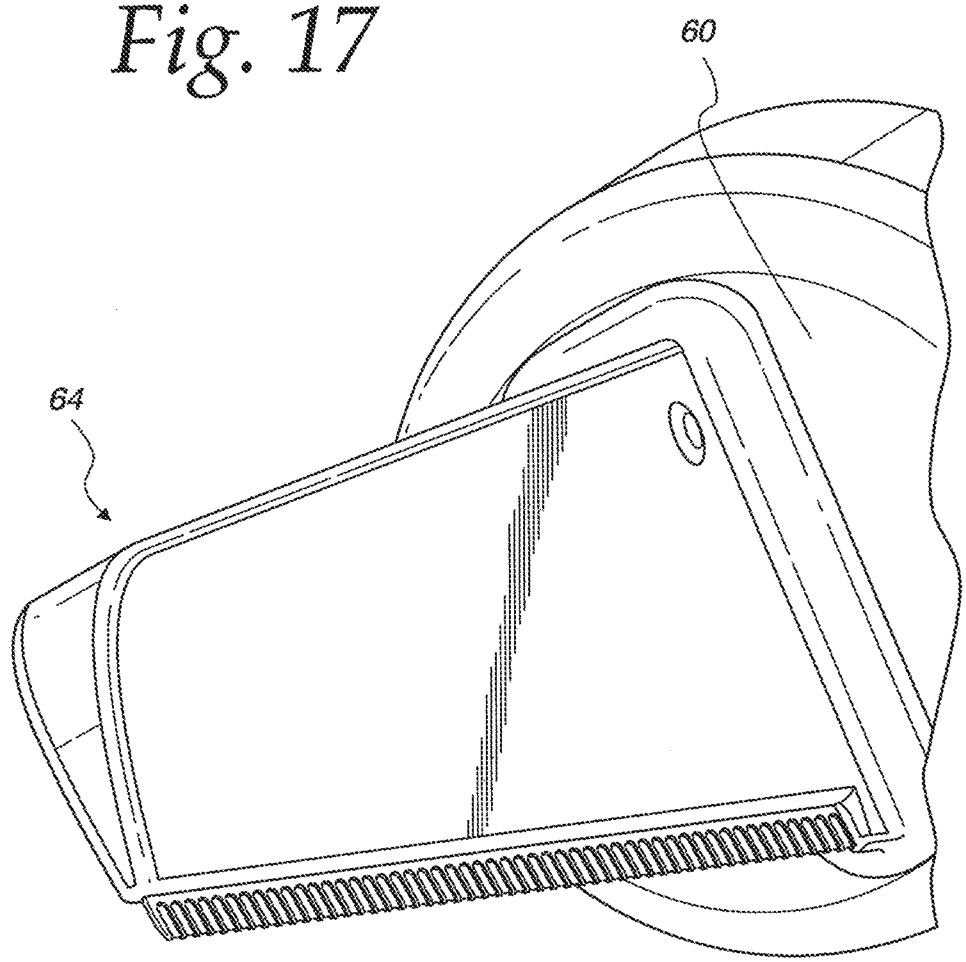
FIG. 17 is a partial isometric view illustrating an exemplary blade assembly with a blade cage.

One end 46 of the main housing 28 may be formed with a reduced diameter cylindrical portion 48 which accomplishes several functions. First, as best shown in FIG. 3, an interior portion of the reduced diameter cylindrical portion 48 is configured to provide a friction fit for the piezoelectric crystal 32. Second, as best shown in FIG. 17, the exterior portion of the reduced diameter cylindrical portion 48 provides a bayonet interface for an exemplary replaceable blade 50 mounted with a bayonet interface that cooperates with the bayonet interface on the exterior portion of the reduced diameter portion 48. In accordance with an important aspect of the invention, a safety cage 66 (FIG. 16*a*) fits over the blade 50 to limit the penetration of the blade 50 into the facial skin.

Turning to FIG. 3, a sectional view of the first embodiment of the dermaplaning device 85, is illustrated. FIG. 3 illustrates the main housing 26 in detail and how all of the various components fit into it. As shown, the various components may be wired and connected, for example, by soldering to the printed circuit board 45.

As mentioned above, this embodiment includes a piezo-electric crystal for vibrating the blade 46 at an ultrasonic frequency defining an ultrasonic mode of operation. The device may also include a DC motor with at least one eccentric rotary loads, generally identified with the reference numeral 51 for generating a vibration frequency other than an ultrasonic vibration frequency defining a sub-ultrasonic frequency mode. The eccentric may be formed as a semi-circular disc 51. A stationary bearing 53 may be disposed axially outwardly from the disc 51 to stabilize the motor shaft 32. Depending on the speed of rotation of the motor shaft, a vibration will be created which will be transmitted to the blade assembly 50.

Driver circuits that drive piezo-electric crystals to generate ultrasonic sound waves/vibrations are well known in the art. Such circuits normally include an alternating current or voltage applied to the piezo-electric crystal. Examples of such driver circuits are disclosed in U.S. Pat. Nos. 3,509,626; 3,967,143 and US Patent Application Publication No. US 2003/0233085 A1. Such a driver circuit is also disclosed in South Korean patent publication no. KR 2004 0022550, all incorporated herein by reference. All references to a piezo electric devices are to be understood to include the driver circuit that causes the piezoelectric device to generate ultrasonic sound waves/vibrations. The driver circuit including its respective components may be disposed on the printed circuit board 45.

Figure 4D:
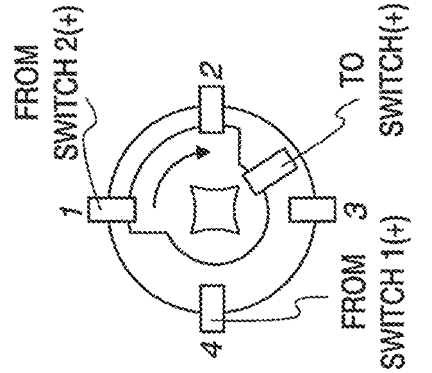
FIGS. 4A-4D is an exemplary schematic of a 4 phase rotary electric switch for use with the present invention, wherein FIG. 4A discloses an OFF position.
Figure 4C:
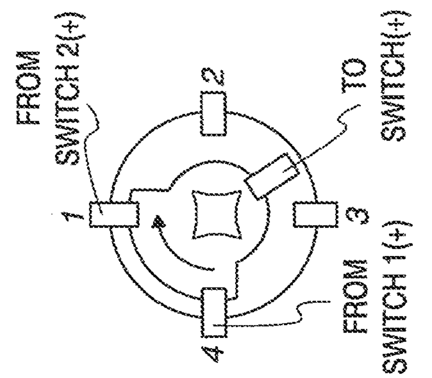
Figure 4B:
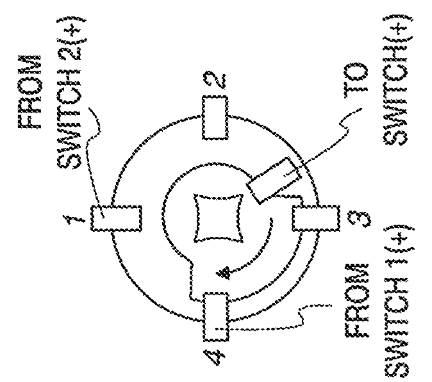
Figure 4A:
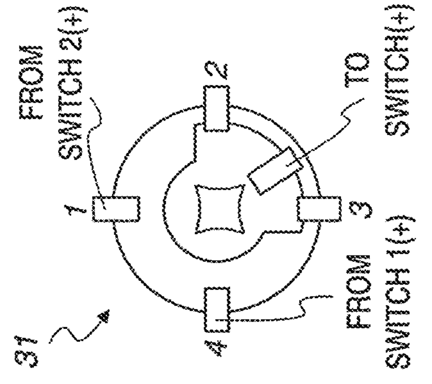
Figure 5:
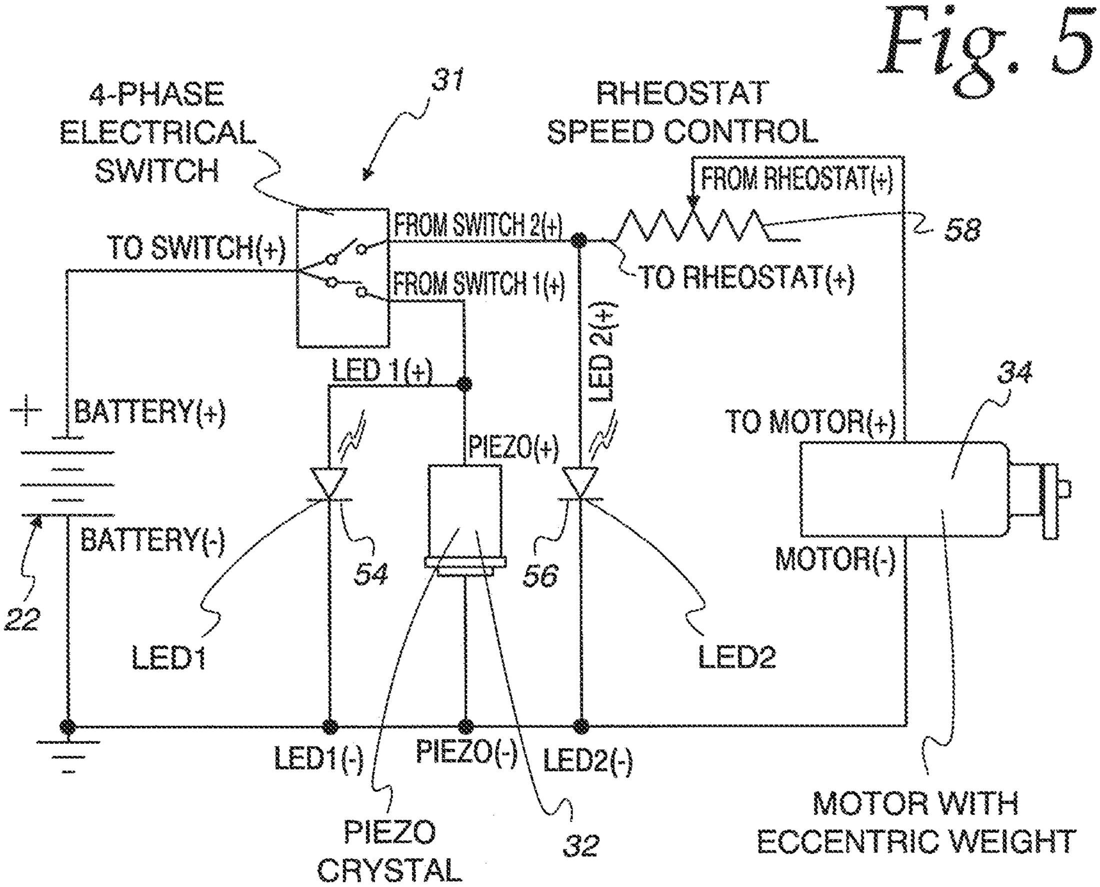
FIG. 5 is an exemplary schematic for the dermaplaning device illustrated in FIG. 3 illustrating an embodiment that includes a piezoelectric crystal, a motor with an eccentric load and an optional rheostat for controlling the speed of the motor.
Figure 6:
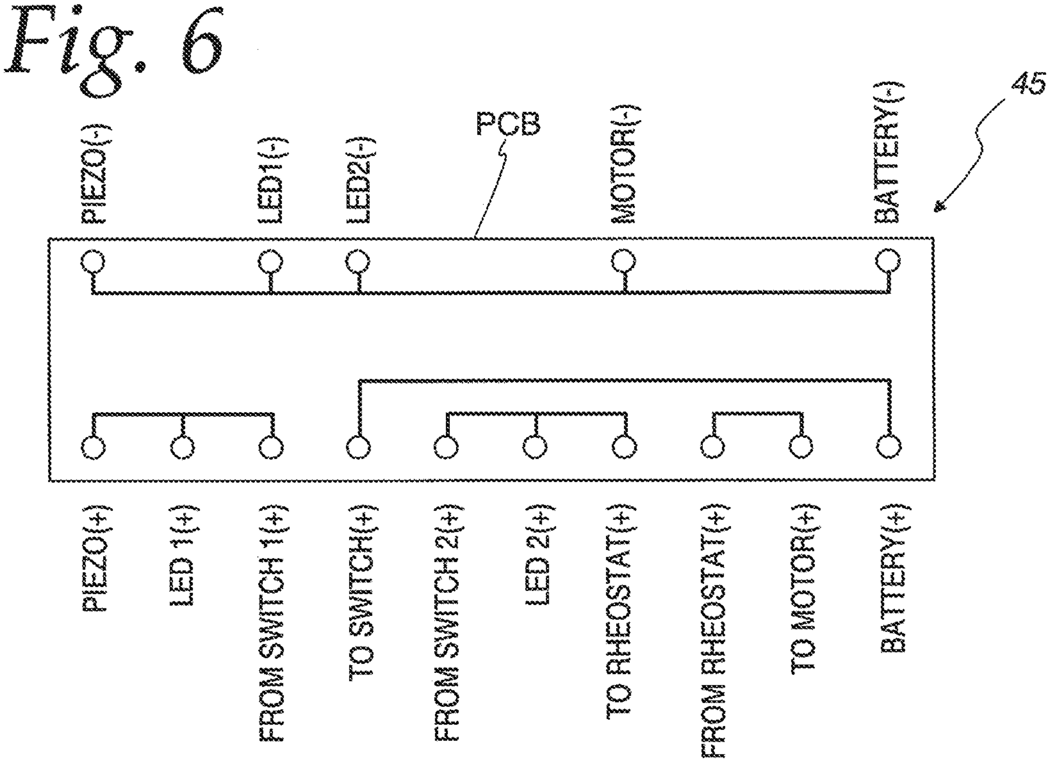
FIG. 6 is a top plan view of an exemplary printed circuit board for use with the embodiment illustrated in FIG. 5.

FIGS. 4-6 illustrate the electrical details for controlling a device 50 that includes a piezoelectric element 32 and a DC motor 34 with at least one eccentric rotary load 51. A key aspect of the control is an optional exemplary 4-position rotary switch 31, as illustrated in FIGS. 4*a*-4*d*. Such 4 position switches are commonly available and include 4 wires. Normally open rotary contacts are provided between terminals 3 and 4 for controlling power to the piezo-electric crystal 32 and between terminal 1 and 2 for controlling power to the DC motor 34. The terminals 2 and 3 are connected together and to the positive terminal of the battery 22.

In a first position of the rotary switch 31, as shown in FIG. 4*a*, the contact between terminals 3 and 4 for controlling the power to the piezo-electric crystal 32 is open as is the contact between the terminals 1 and 2 for controlling power to the DC motor 34 is open. As such in the position illustrated in FIG. 4*a*, no power is delivered to either the piezo-electric crystal 32 or the motor 34. In a second position of the rotary switch 31, as illustrated in FIG. 4*b*, the contact between the terminals 3 and 4 is closed, thus providing power, i.e. connecting the .+−.battery terminal, to the piezoelectric crystal 32. Since the contact between the terminals 1 and 2 is open, no power is delivered to the motor 34 when the switch 31 is in the position, as illustrated in FIG. 4*b*. FIG. 4*c* illustrates another OFF position in which the contact between the terminals 3 and 4 and the contact between the terminals 1 and 2 are both open, thus disconnecting the power from both the piezo-electric crystal 32 and the motor 34. FIG. 4*d* illustrates a position of the switch 31 in which the contact between the terminals 1 and 2 is closed thus providing power to the motor 34. Since the contact between terminals 3 and 4 is open in this position, no power is delivered to the piezoelectric crystal 32 in this position.

An exemplary schematic diagram for the dermaplaning device 85 is illustrated in FIG. 5. As shown, the circuit is powered by the battery 22. As discussed above, the rotary switch 31 enables the battery 22 to be selectively connected to the piezo-electric crystal 32 or alternatively to motor 34 defining an ultrasonic mode or a sub-ultrasonic frequency mode, respectively. Optional LEDs 54 and 56 may be provided to indicate the mode of the device 50. In particular, the LED 54 is connected in parallel with the piezo-electric crystal 32. Thus, any time the piezo-electric crystal 32 is connected to the positive terminal of the battery 22, the LED 54 is illuminated indicating that the device 50 is operating in an ultrasonic mode of operation. Similarly the optional LED 56 is connected essentially in parallel with the motor 34.

Thus, any time the motor 34 is connected to the positive terminal of the battery 22, the LED 56 will be illuminated indicating a sub-ultrasonic mode of operation. Both LEDs 54 and 56 will be off when neither the piezoelectric crystal 32 nor the motor 34 are connected to the positive terminal of the battery 22.

Figure 1:
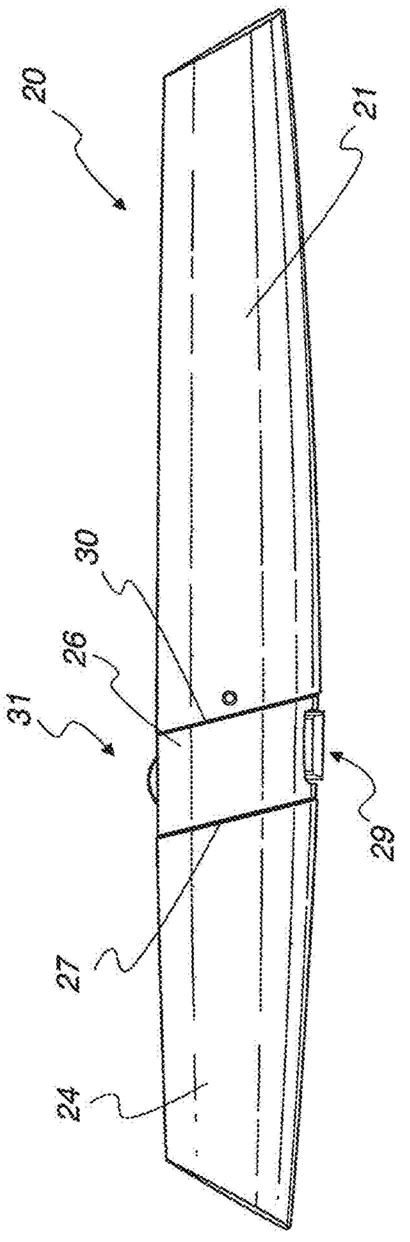
FIG. 1 is a side elevational view of an exemplary dermaplaning device in accordance with one embodiment of the device which includes a vibration generator which includes a piezo-electric crystal and a motor with an eccentric load.
Figure 2:
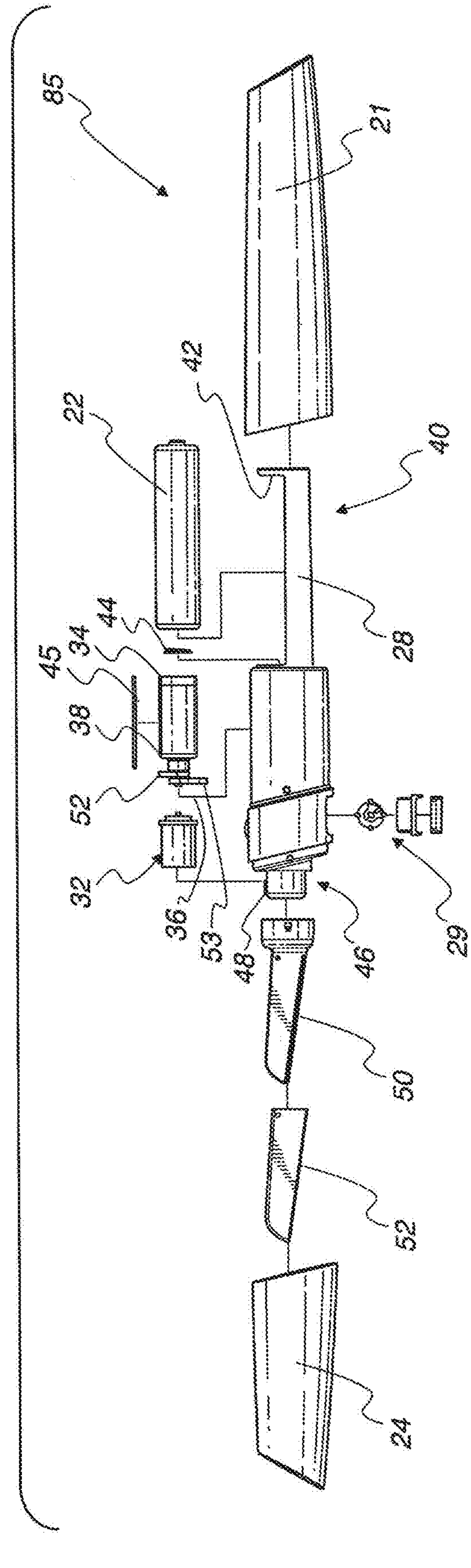
FIG. 2 is an exploded view of one embodiment of the dermaplaning device illustrated in FIG. 1.

An optional rheostat 58 may be connected in series with the motor 34. As is known in the art, the speed of a DC motor can be control the voltage applied to the motor. The optional rheostat 58 is adjustable and can be controlled to vary its resistance, which, in turn, varies the current and voltage to the motor 34. By varying the speed of the motor 22, the vibration frequency can be varied. As shown in FIG. 1, an optional thumb wheel 31 is accessible from outside the housing 20 to allow the rheostat 58 to be adjusted. The motor 34 may be operated at 600 RPM, for example.

FIG. 6 is an optional and exemplary printed circuit board 45 which may be used to connect the various components to the circuit. It is contemplated that the configuration of the printed circuit board 45 may be different from that shown. Also, various conventional techniques are contemplated for connecting the various components to the printed circuit board 45. One such technique is soldering. Alternatively, the printed circuit board 45 can be omitted and connections between the various components be made with electrical wires. It is also contemplated that the rotary switch 31, as well as the optional LEDs 54 and 56 and the optional rheostat 58 can be mounted on the printed circuit board 45.

Second Embodiment

Figure 10:
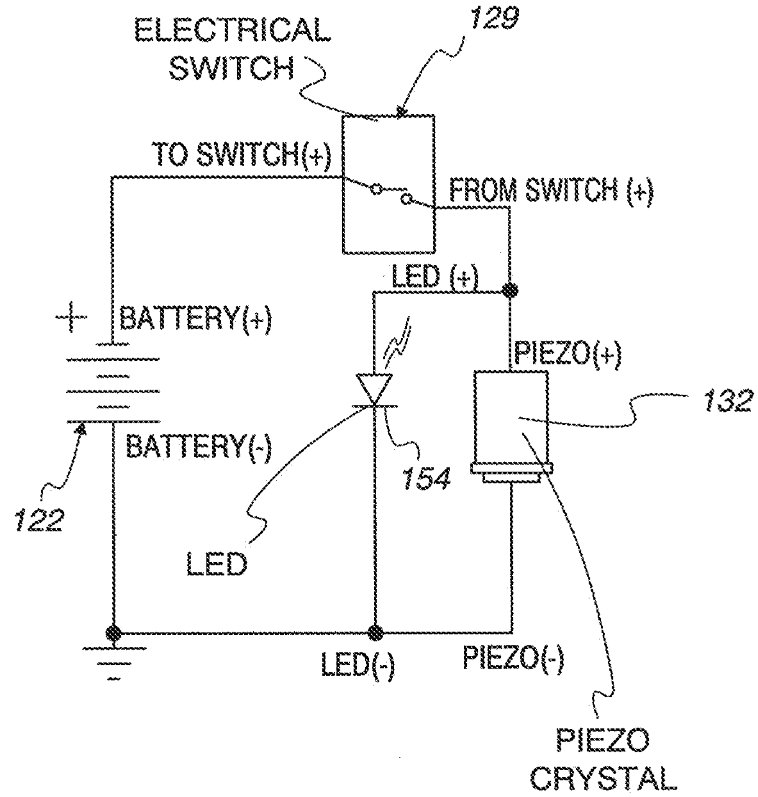
FIG. 10 is an exemplary schematic diagram of the dermaplaning device illustrated in FIG. 8.
Figure 11:
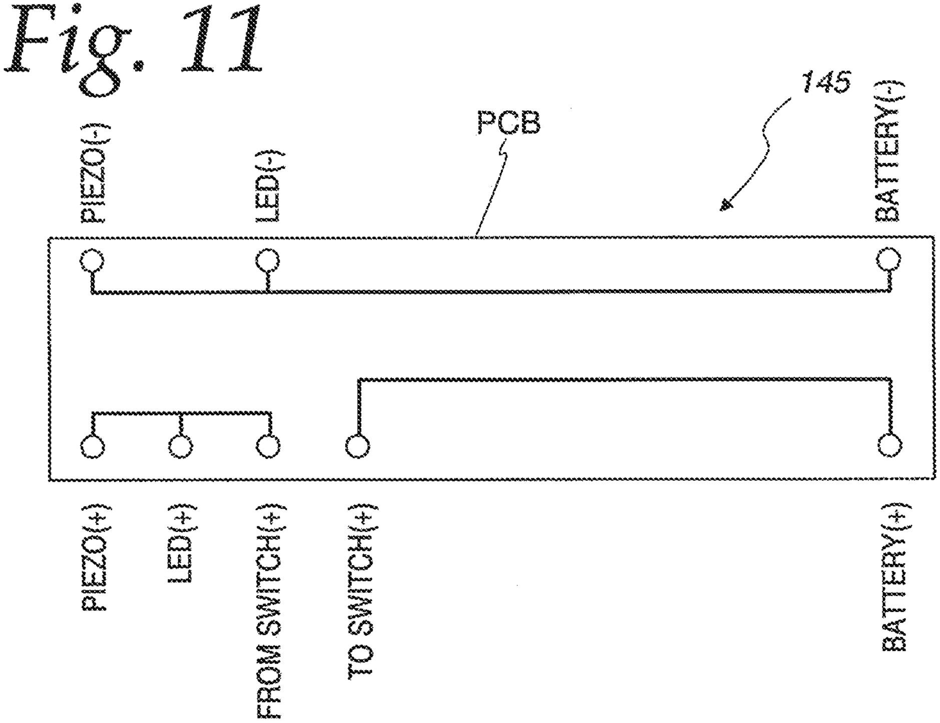
FIG. 11 is an exemplary printed circuit board for use with the dermaplaning device illustrated in FIG. 8.

The second embodiment is illustrated in FIGS. 8-11 and identified with the reference number 185. In this embodiment, like components are identified with like reference numerals with a 1 prefix. In this embodiment, the dermaplaning device 185 only includes a piezoelectric crystal 132. As shown in FIG. 10, a simple single pole single throw micro switch 129 may be used to control the piezo-electric vibration device 132. An optional LED 154 may be included as part of the micro switch 129. A printed circuit board 145 may be provided for making the connections between the various devices. Moreover, the micro switch 129 may be mounted to the printed circuit board 145.

Third Embodiment

Figure 14:
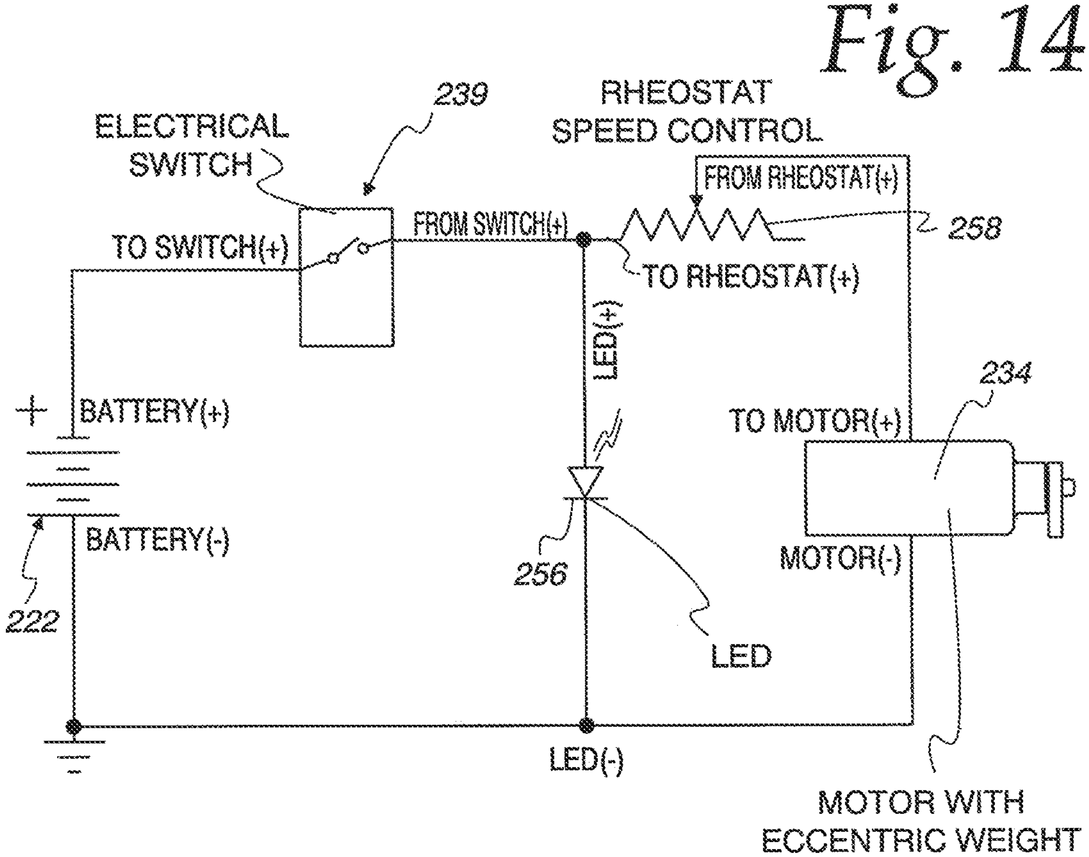
FIG. 14 is an exemplary schematic diagram of the dermaplaning device illustrated in FIG. 12.
Figure 15:
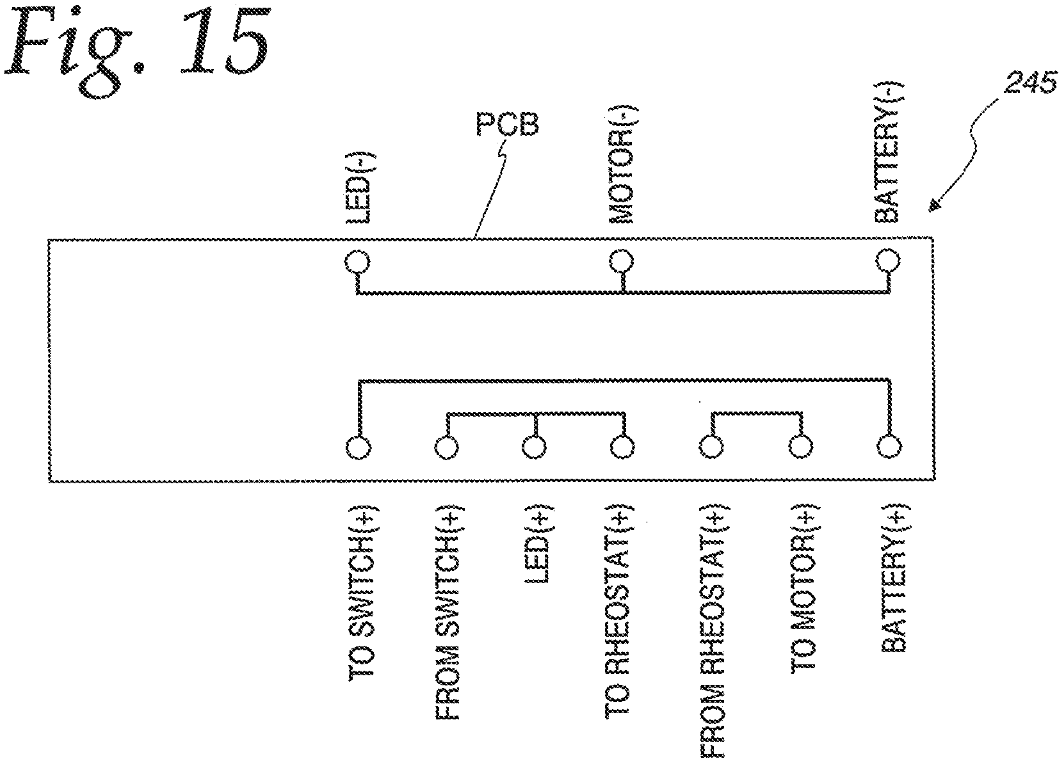
FIG. 15 is an exemplary printed circuit board for use with the dermaplaning device illustrated in FIG. 1.

The third embodiment is illustrated in FIGS. 12-15 and identified with the reference numeral 285. In this embodiment, like components are identified with like reference numerals with a 2 prefix. In this embodiment, the dermaplaning device 285 only includes a motor 234 and the eccentric rotary load 249 supported by a bearing 253. As shown in FIG. 14, a simple single pole single throw micro switch 229 may be used to control power to the motor 234. An optional LED 256 may be included as part of the micro switch 229. In addition, an optional rheostat 258 may be provided for controlling the speed of the motor 234. As shown best in FIG. 13, the rheostat 258 includes a thumb wheel 231. The thumb wheel 231 may optionally be mounted as shown in FIG. 1 to enable adjustment of the motor speed from the outside of the device 250. to A printed circuit board 245 may be provided for making the connections between the various devices. Moreover, the micro switch 229 may be mounted to the printed circuit board 245.

Figure 12:
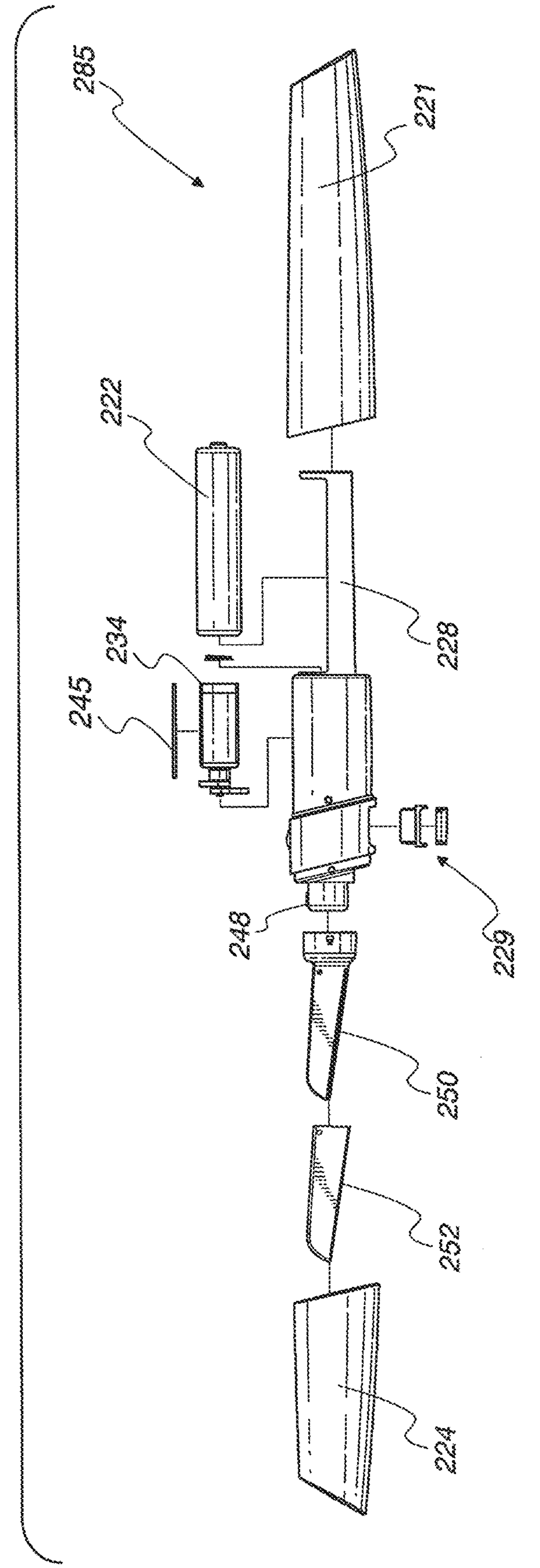
FIG. 12 is an exploded view of another alternate embodiment of a dermaplaning device that only includes a motor and an eccentric load.
Figure 13:
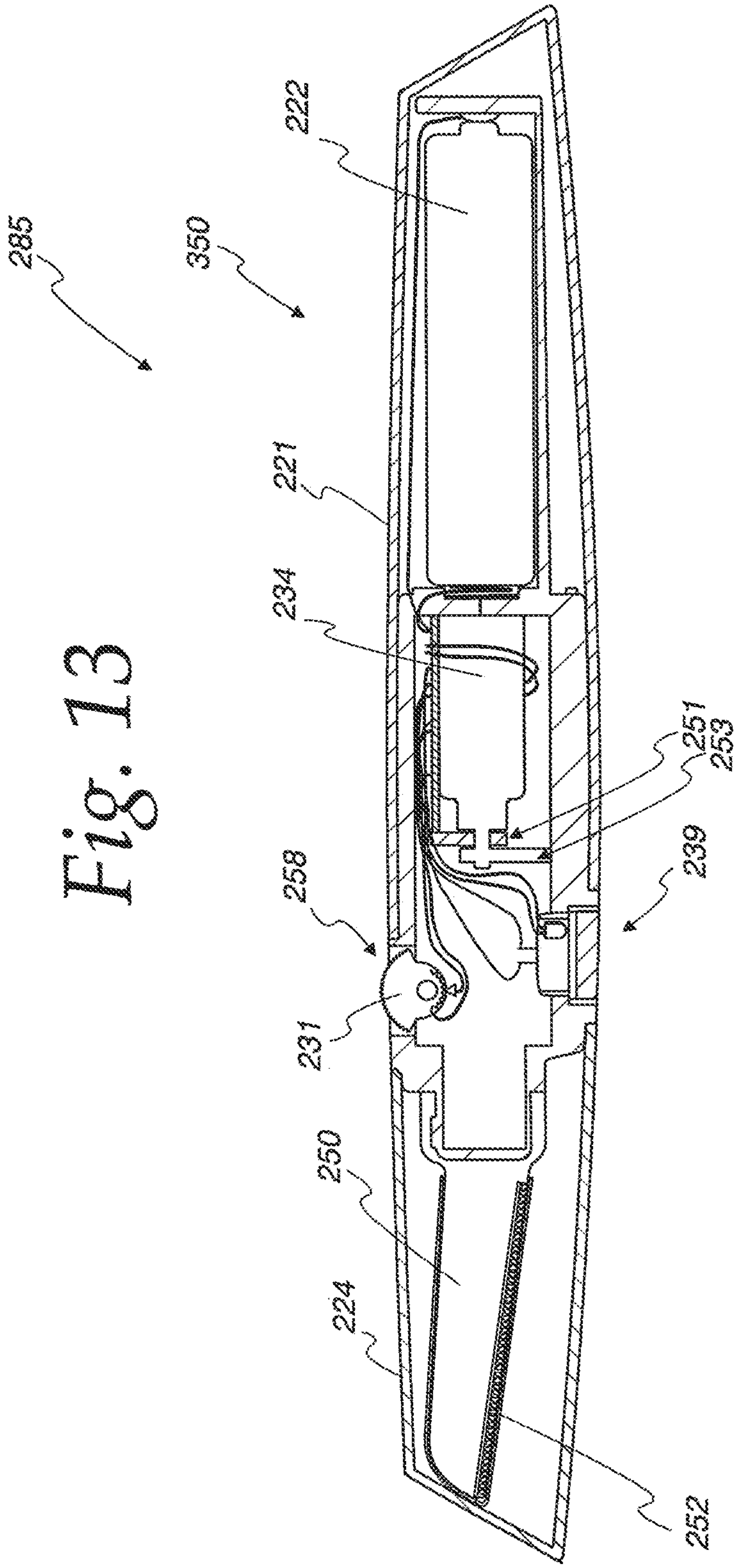
FIG. 13 is side elevational view in section of the dermaplaning device illustrated in FIG. 12.
Figure 13A:
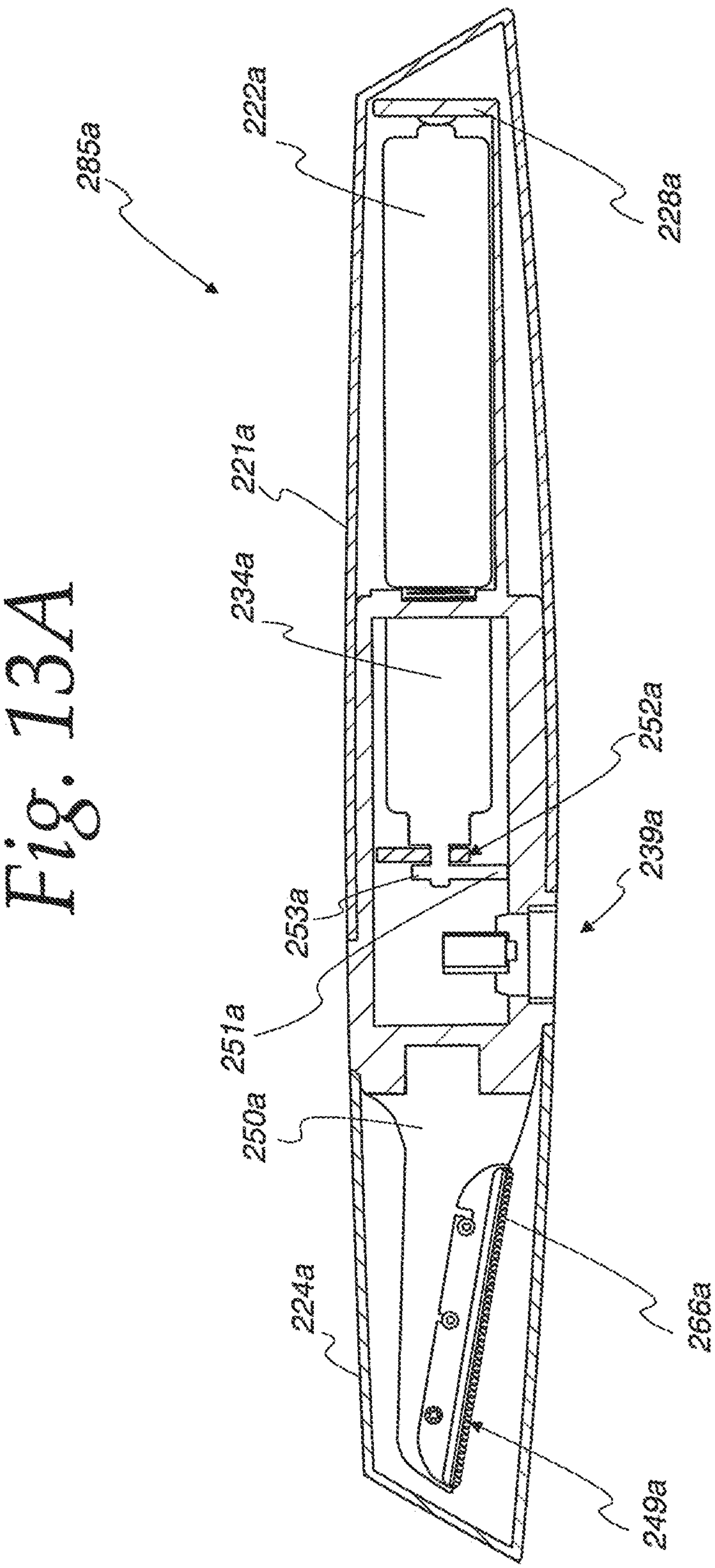
FIG. 13A is an alternate embodiment of the device illustrated in FIG. 12 illustrating a removable blade.

An alternate embodiment of the embodiment in FIG. 12 is illustrated in FIG. 13*a*. In this embodiment, like reference numerals with an "a" suffix are used to identify like parts. In this embodiment no rheostat is provided. Also, in this embodiment as well as the embodiment illustrated in FIGS. 12-15, the printed circuit board may be eliminated. In this embodiment as well as the other embodiments, the blade or scalpel 250*a* can be bayonet mounted or fixedly mounted to the housing 228*a*.

In all of such embodiments, the scalpel or blade 250*a* can be a one piece blade and configured with a bayonet mount, as illustrated and described above. Alternatively, the blade 250*a* can be formed as a 2 piece device; namely a scalpel 250*a* with a removable blade 249*a*, as shown in FIG. 13*a*. In such an embodiment, the scalpel 250*a* may be fixedly mounted to the housing 228*a*. Other configurations of a scalpel with a removable blade are also considered to be within the broad scope of the claims.

Scalpels with removable blades are extremely well known in the art. An example of a scalpel with a removable blade is illustrated and described in detail in U.S. Pat. No. 1,139,796, hereby incorporated by reference. In embodiments with a removable blade 249*a*, a safety cage 266*a*, as discussed above, may be formed on the blade 249*a*. The device illustrated in FIG. 13*a* may also include a safety cover, for example, a safety cover (not shown) similar to the safety cover 252 as shown in FIG. 12 which fits over the scalpel 250*a* and the removable blade 249*a*.

Figure 13C:
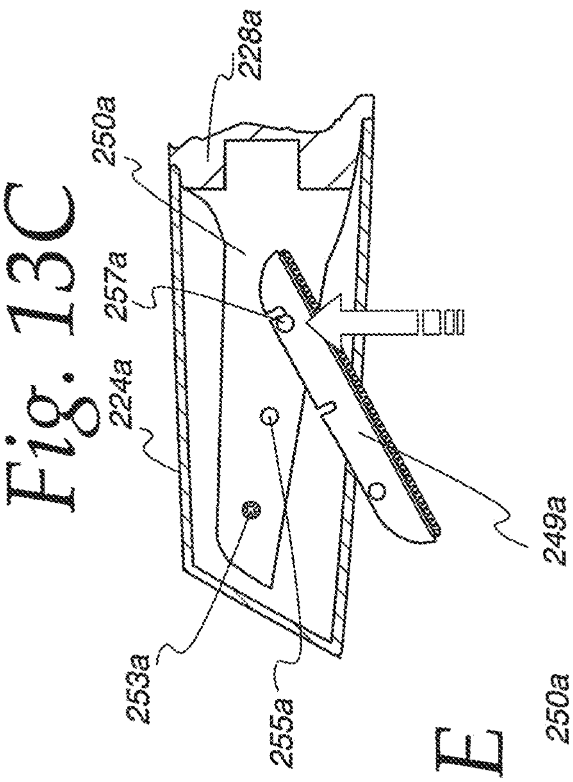
FIGS. 13B, 13C and 13D illustrate how the removable blade is attached to the scalpel.
Figure 13F:
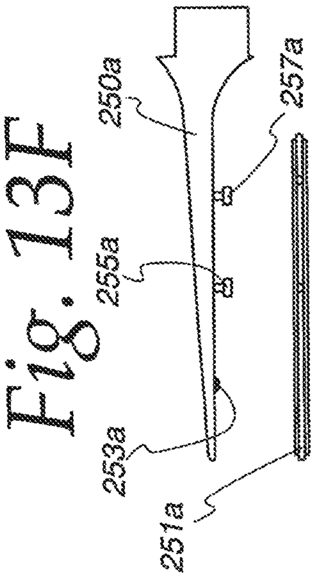
FIG. 13F is similar to FIG. 13E but illustrating the removable blade removed from the scalpel.
Figure 13E:
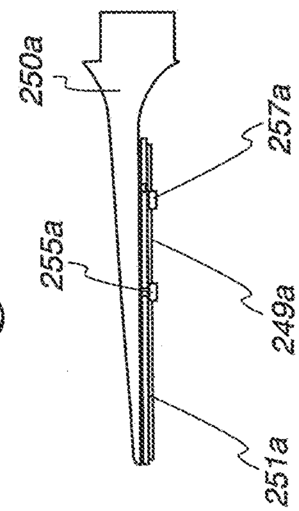
FIG. 13E is a side elevational view illustrating the removable blade attached to the scalpel.
Figure 13B:
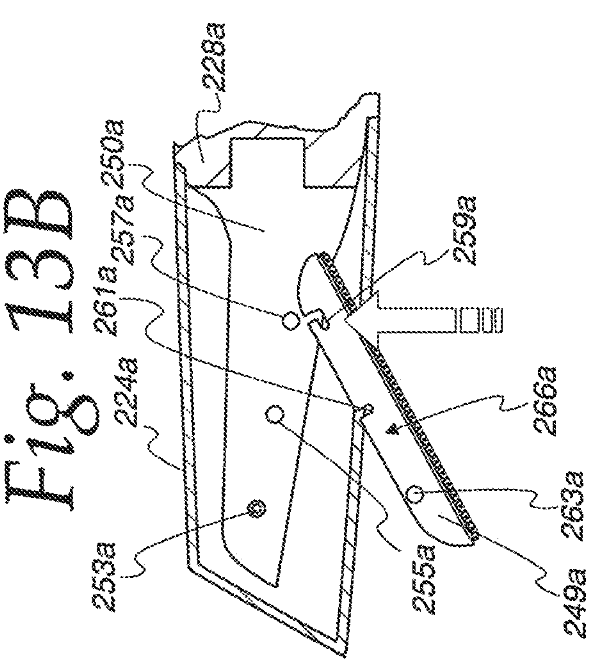
Figure 13D:
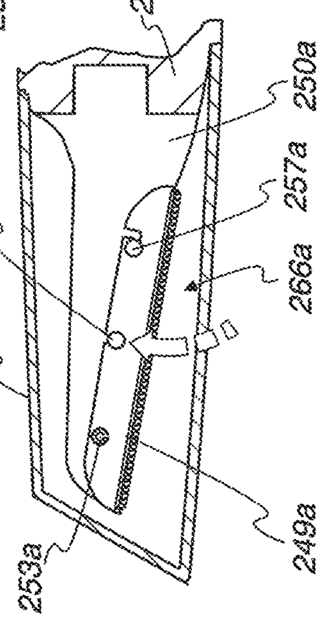

FIG. 13*a* illustrates the scalpel 250*a* with a removable blade 249*a* attached thereto. FIGS. 13*b*-13*d* illustrate bow the removable blade 249*a* is attached to the scalpel 250*a*. The scalpel 250*a* is formed with a plurality of posts, for example 3 posts, identified with the reference numerals 253*a*, 255*a* and 257*a*. These posts 253*a*, 255*a* and 257*a* are formed on the scalpel and extend outwardly therefrom on one side as shown. These posts 253*a*, 255*a* and 257*a* are formed to co-operate with slots 259*a*, 261*a* and 263*a*, formed in the removable blade 253*a*. As shown best in FIG. 13*b*, the slots 259*a* and 259*b* are open slots and are configured to receive the extending posts 255*a* and 257*a* on the scalpel 250*a*. An aperture 263*a* is formed in the blade 250*a* for receiving the post 253*a* formed on the scalpel 250*a*. As is apparent from FIGS. 13*e* and 13*f*, the post 253*a* is shorter than the posts 255*a* and 257*a*. This feature allows the post 253*a* to snap in place and be received in the aperture 249*a* and essentially lock the blade 249*a* in place with respect to the scalpel 250*a*.

Figure 13G:
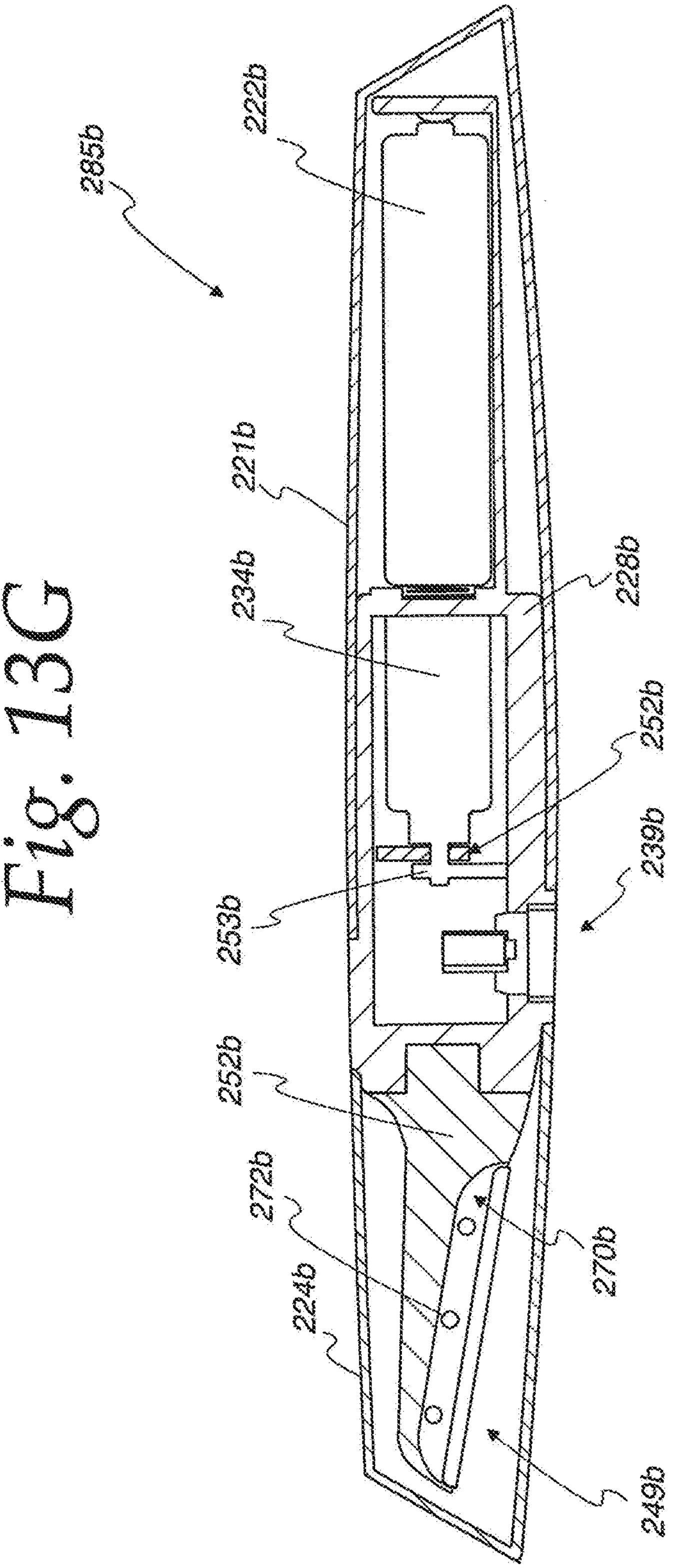
FIG. 13G is another alternate embodiment of the of the device illustrated in FIG. 12.

Another alternate embodiment of the embodiment in FIG. 12 is illustrated in FIG. 13*g*. In this embodiment, like reference numerals with an "b" suffix are used to identify like parts. This embodiment is similar to the embodiment illustrated in FIG. 13*a* except in this embodiment, the device 285 is provided with a one-piece blade 252*b* that attaches to the device by way of a bayonet mount, as discussed above. In this embodiment a blade cover 270*b* is provided. The blade cover 270*b* may be provided with a c-type cross-section and formed with a spring force causing buttons, generally identified with the reference numeral 272*b* to pinch the blade 252*b* once the cover 270*b* is slid over the blade 252*b*.

The Blade

Figure 16:
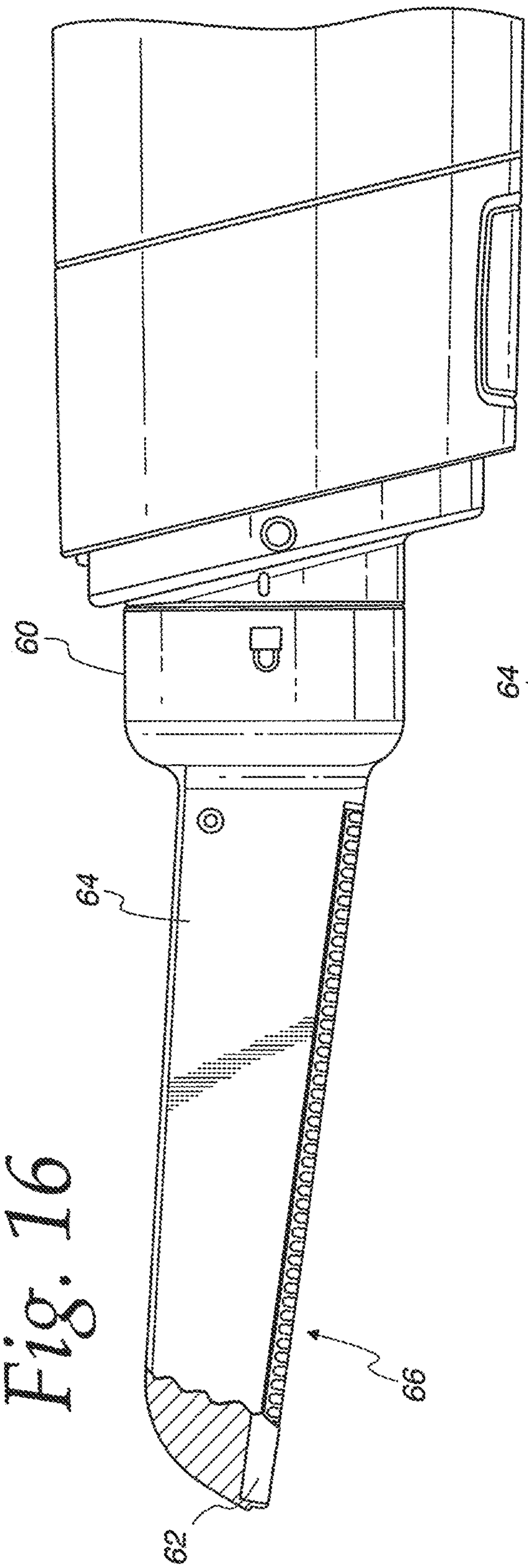
FIG. 16 is a partial side elevational view of the dermaplaning device in accordance with the present invention illustrating the removable blade attached to a handle portion of the housing.
Figure 18:
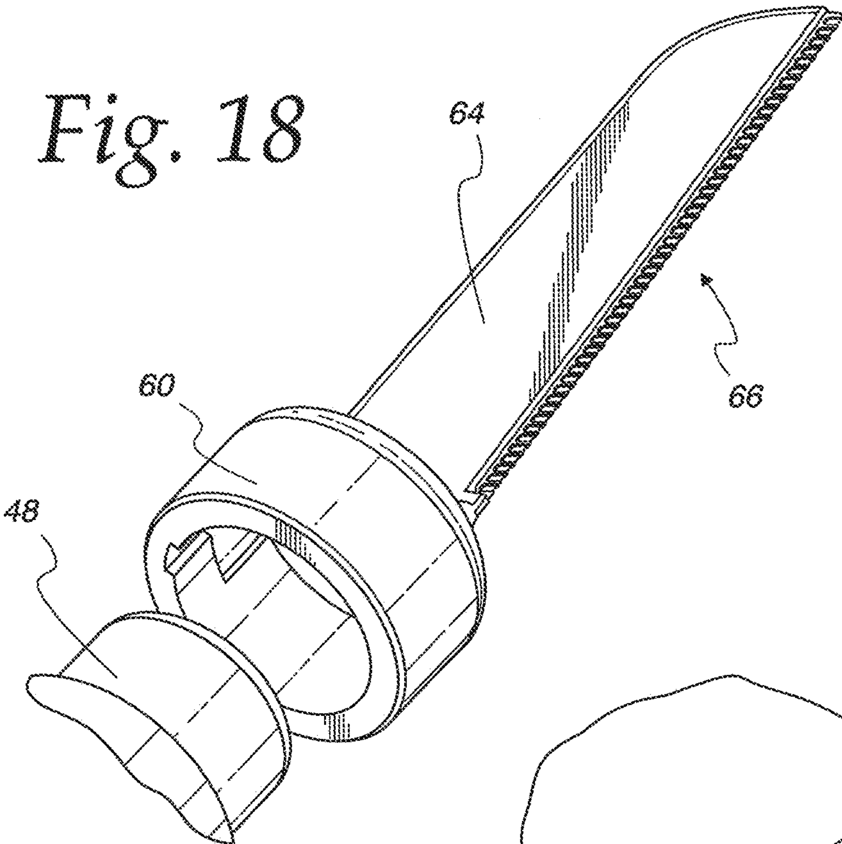
FIG. 18 is a partial isometric view of an exemplary blade assembly, shown removed from the handle portion of the housing illustrating an exemplary bayonet type interface.

An important aspect of the invention relates to the blade assembly 50, 150, 250. The blade assembly 50, 150, 250 is best shown in FIGS. 16-18. As best shown in FIG. 18, the blade assembly 50, 150, 250 is mounted to a generally cylindrical portion 60 and is configured to mate with the cylindrical portion 48 (FIG. 2) attached to the handle portion 21 (FIG. 1). The blade assembly 50, 150, 250 is only used on a single user. As such, the blade 62 assembly 50, 150, 250 is removable for disposal and replaced for each new user and for each use.

As shown in FIGS. 16 and 18, the cylindrical portion 60 of the blade assembly 50. 150, 250 is configured to attach to the cylindrical portion 48 attached to the handle portion 21, for example by way of a bayonet connection. Other connections are also suitable.

In accordance with an important aspect of the invention, the blade assembly 50, 150, 250 includes a surgical blade or scalpel 62 and a molded housing 64, shown best in FIG. 17 with a wedge shaped cross section. The blade 62 extends along an axis generally parallel to or at an acute angle with respect to a longitudinal axis of the device housing 20 (FIG. 1), 23 (FIG. 7). In order to limit the depth of the cut into the skin and to prevent non-professionals from accidentally cutting below the epidermis layer of facial skin, a safety cage 66 is juxtaposed over an extending portion of the blade 62. More particularly, the safety cage 66 extends over a cutting edge 67 of the blade 62 and extends from the blade housing 64. As best shown in FIG. 16*a*, the safety cage 66 is formed as an exemplary comb-like structure defining posts 68 and valleys 70. The comb-like structure 66 may be injection molded over the cutting edge 67 of the blade 62. Alternatively, the comb-like structure 66 may be snapped in place over the cutting edge 67 of the blade 62. The depth of the valleys 70 limits the depth of the cut by limiting the depth of the valleys 70, for example, to several millimeters. As such, the blade assembly 50, 150, 250 is rendered safe for use by non-professionals as a part of a dermaplaning device.

As mentioned above, two piece blades or scalpels may be used. In such embodiments, the safety cage is provided over the cutting edge portion of the removable blade.

Process

A process for treating facial skin is described for non-professionals. An exemplary process for treating facial skin by the non-professional is discussed below which includes dermaplaning.

1. Cleanse: This step prepares the skin for the dermaplaning procedure. It effectively removes makeup as well as product residue, while ridding the skin of surface oils. Moisten face with warm water, apply a small amount of cleanser to moist palm, form lather with hands and massage onto face. Rinse with warm water and repeat. Blot skin dry 2. Dermaplane: Use a hand-held dermaplaning device which includes a blade and embedded vibration technology, for example, as disclosed above, that is safe for use by non-professionals which safely exfoliates the skin. Dermaplaning devices with a blade and embedded vibration technology other than the one described herein are also suitable. The vibration technology maximizes the blades efficiency while stimulating micro circulation and lymphatic activity. Skin is not only deeply exfoliated, but all traces of built up debris and vellus hair are removed. Skin is left baby soft, product penetration is maximized.

Begin by grasping the and switching on the device. A subtle vibration will immediately be noticed.

Figure 19:
FIG. 19 illustrates a partial isometric view of a person using the dermaplaning device in accordance with the present invention.
Figure 20:
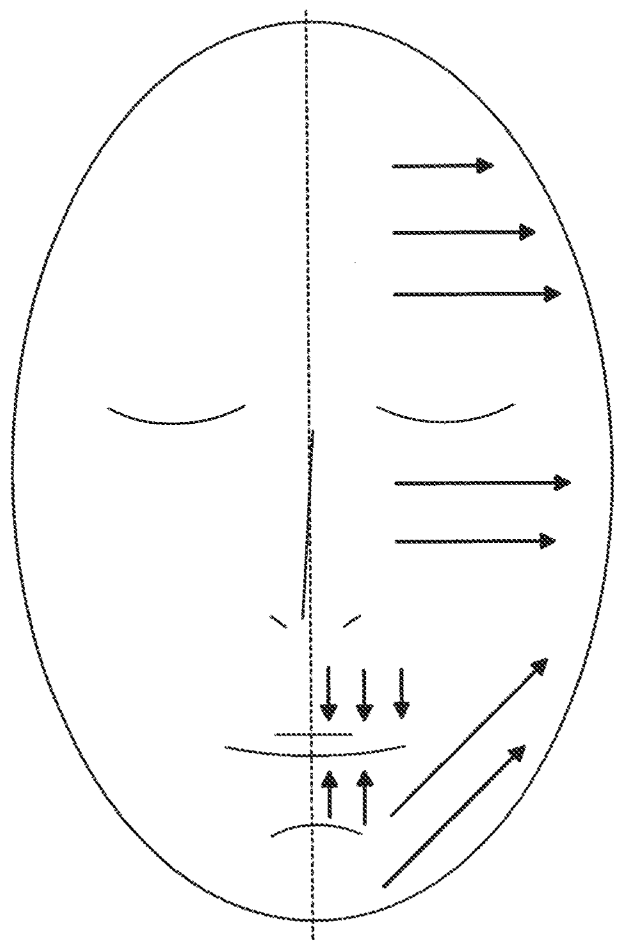
FIG. 20 is drawing of a face with the arrows illustrating the direction of the strokes of the dermaplaning device on a user's face.

As illustrated in FIGS. 19 and 20, begin the treatment at the center of face focusing on right side, using gentle yet firm pressure, move the device across forehead and towards hair line, following the contours of your face, avoiding the brow and eye area.

Once you have completed the upper face move to the lower face and begin again at the centerline using the same gentle but firm pressure moving the device along the jawline up toward the ear. Continue working up and onto the cheek moving from the nose toward the ear following the contour of the cheek. The nose and eye area should be avoided. When working around the mouth use short strokes with gentle yet firm pressure and move toward the vermillion border (edge of lip) and avoid the surface of the lip.

The dermaplaning device is very efficient at exfoliating the skin and no more than two passes in any area are necessary. When the right side of the face is completed, move to the left side, following the same pattern.

3. Peel A chemical peel completes the exfoliation process. Various chemical peels are suitable. For example, a chemical peel comprising a blend of alpha and beta hydroxy acids combined with an anti-oxidant compound, for example, Bioperfect's Anti-Oxidant Complex, completes the exfoliation process and amplifies cellular turnover to help stimulate production of collagen. This peel is to be used immediately following the use of the dermaplaning device.

Open prepared peel pad. Begin on forehead, apply peel to entire face and neck beginning on forehead and using a circular motion. Avoid contact with delicate eye and lip areas.

4. Post Treatment Comforting Balm—Use a balm that has been specifically formulated to comfort, nourish, and protect delicate post treatment skin. The balm is absorbed deeply into newly exfoliated skin, leading to optimum absorption of our proprietary multi-dimensional complex of cosmeceuticals.

Use a small amount and massage into face and neck avoiding eye area.

Obviously, many modifications and variations of the present invention are possible in light of the above teachings. Thus, it is to be understood that within the scope of the appended claims, the invention may be practiced otherwise than as specifically described above.

What is claimed is:

1. A blade kit for a hand-held skin treatment device, the skin treatment device including an elongate handle with a head at a distal end thereof for connecting with a blade assembly, the blade kit comprising:

a blade retainer including a plurality of elongated retainer slots arranged adjacent each other in a side-by-side arrangement, each retainer slot extending in a longitudinal direction;

a plurality of blade assemblies positioned in the plurality of retainer slots, each blade assembly including a pair of connectors configured to detachably connect the blade assembly to the head of the skin treatment device, each blade assembly further including opposite sides extending in the longitudinal direction and a notch located on a side thereof, each blade assembly further including only one blade, the blade being centered between the opposite sides thereof, the blade including a cutting edge extending in the longitudinal direction, the cutting edge being centered between the opposite sides of the blade assembly; and a blade assembly retainer located at a side of each retainer slot, the blade assembly retainer cooperating with the notch to releasably retain the blade assembly in the retainer slot, the blade being positioned between the blade assembly retainer and an opposite side of the retainer slot.

2. The blade kit according to claim 1, wherein the notch is configured to be located between the head of the skin treatment device and the cutting edge when the blade assembly is connected to the head.

3. The blade kit according to claim 1, wherein the blade assembly includes a safety cage adjacent the blade, the safety cage configured to limit penetration of the blade into the skin.

4. The blade kit according to claim 3, wherein the safety cage includes a plurality of teeth protruding a distance beyond the cutting edge.

5. The blade kit according to claim 4, wherein the safety cage includes a first cage portion and a second cage portion, the blade being located between the first and second cage portions.

6. The blade kit according to claim 5, wherein the blade includes a first side and a second side, the first cage portion located adjacent the first side of the blade and the second cage portion located adjacent the second side of the blade.

7. The blade kit according to claim 1, wherein the blade assembly retainer is configured to release the blade assembly from the retainer slot in response to application of an upward force to the blade assembly away from the retainer slot.

8. The blade kit according to claim 1, wherein the blade retainer includes six retainer slots with a corresponding blade assembly retained therein.

9. The blade kit according to claim 1, wherein each blade assembly is oriented in the blade retainer to enable the blade assembly to be loaded directly onto the skin treatment device without requiring a user to touch the blade assembly.

* * * * *